(12) United States Patent
Lai et al.

(10) Patent No.: US 6,407,135 B1
(45) Date of Patent: *Jun. 18, 2002

(54) CONJUGATES OF DITHIOCARBAMATES WITH PHARMACOLOGICALLY ACTIVE AGENTS AND USES THEREFOR

(75) Inventors: Ching-San Lai, Encinitas; Tingmin Wang, San Marcos, both of CA (US)

(73) Assignee: Medinox, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/453,608

(22) Filed: Dec. 3, 1999

Related U.S. Application Data

(63) Continuation-in-part of application No. PCT/US98/10295, filed on May 19, 1998, which is a continuation of application No. 08/869,158, filed on Jun. 4, 1997, now Pat. No. 5,916,910.

(51) Int. Cl.$^7$ .................... C07D 207/04; C07D 207/30; A61K 38/00; A61K 31/27; A61K 31/40
(52) U.S. Cl. .......................... 514/423; 514/2; 514/514; 530/402; 548/565; 548/573
(58) Field of Search ................................. 530/402, 300, 530/356; 514/8–25, 2, 423, 514; 548/565, 573

(56) References Cited

U.S. PATENT DOCUMENTS

| | | | |
|---|---|---|---|
| 4,160,452 A | 7/1979 | Theeuwes | 128/260 |
| 4,256,108 A | 3/1981 | Theeuwes | 128/260 |
| 4,265,874 A | 5/1981 | Bonsen et al. | 424/15 |
| 5,916,910 A | * 6/1999 | Lai | 514/423 |

OTHER PUBLICATIONS

Asako et al., "Indomethacin–induced leukocyte adhesion in mesenteric venules: role of lipoxygenase products," *The American Physiological Society*, 903–908, 1992.
Bjarnason et al., "Side Effects of Nonsteroidal Anti–inflammatory Drugs on the Small and Large Intestine in Humans," *Gastroenterology*, 104:1832–1847, 1993.
Carson et al., "The Relative Gastrointestinal Toxicity of the Nonsteroidal Anti–inflammatory Drugs," *Arch Intern Med*, 147:1054–1059, 1987.
Glaser et al., "Etodolac selectively inhibits human prostaglandin G/H synthase 2 (PGHS–2) versus human PGHS–1," *European Journal of Pharmacology*, 281:107–111, 1995.
Iademarco et al., "Characterization of the Promoter for Vascular Cell Adhesion Molecule–1 (VCAM–1)," *The Journal of Biological Chemistry*, 267/23:16323–16329, 1992.
Jones and Cherian, "The search for chelate antagonists for chronic cadmium intoxication," *Toxicology*, 62:1–25, 1990.
Kargman et al., "Characterization of Prostaglandin G/H Synthase 1 and 2 in Rat, Dog, Monkey, and Human Gastrointestinal Tracts," *Gastroenterology*, 111:445–454, 1996.

Meade et al., "Differential Inhibition of Prostaglandin Endoperoxide Synthase (Cyclooxygenase) Isozymes by Aspirin and Other Non–steroidal Anti–inflammatory Drugs*," *The Journal of Biological Chemistry*, 268/9:6610–6614, 1993.
Middleton et al., "Increased nitric oxide synthesis in ulcerative colitis," *The Lancet*, 341:465–466, 1993.
Mitchell et al., "Selectivity of nonsteroidal antiinflammatory drugs as inhibitors of constitutive and inducible cyclooxygenase" *Proc. Natl. Acad. Sci. USA*, 90:11693–11697, 1994.
Onoe et al., "IL–13 and IL–4 Inhibit Bone Resorption by Suppressing Cyclooxygenase–2–Dependent Prostaglandin Synthesis in Osteoblasts," *The Journal of Immunology*, 758–764, 1996.
Myers, "Adriamycin: The Role of Lipid Peroxidation in Cardiac Toxicity and Tumor Response," *Science*, 197:165–167, 1977.
Reisinger et al., "Inhibition of HIV progression by dithiocarb," *The Lancet*, 335:679–682, 1990.
Shreck et al., "Dithiocarbamates as Potent Inhibitors of Nuclear Factor κB Activation in Intact Cells," *J. Exp. Med.*, 175:1181–1194, 1992.
Slater et al., "Expression of cyclooxygenase types 1 and 2 in human fetal membranes at term," *Am. J. Obstet. Gynecol.*, 172/1:77–82, 1995.
Soll et al., "Nonsteroidal Anti–inflammatory Drugs and Peptic Ulcer Disease," *Annals of Internal Medicine*, 114:307–319, 1991.
Graham et al., "Nonsteroidal anti–inflammatory effect of sulindac sulfoxide and sulfide on gastric mucosa," *Clin. Pharmacol. Ther.*, 38/1:65/70, 1985.
Sunderman, "Clinical Response to Therapeutic Agents in Poisoning from Mercury Vapor," *Annals of Clinical And Laboratory Science*, 8/4:259–269, 1978.

(List continued on next page.)

*Primary Examiner*—Avis M. Davenport
(74) *Attorney, Agent, or Firm*—Stephen E. Reiter; Foley & Lardner

(57) ABSTRACT

In accordance with the present invention, there are provided conjugates of nitric oxide scavengers (e.g., dithiocarbamates, or "DC") and pharmacologically active agents (e.g., NSAIDs). Invention conjugates provide a new class of pharmacologically active agents (e.g., anti-inflammatory agents) which cause a much lower incidence of side-effects due to the protective effects imparted by modifying the pharmacologically active agents as described herein. In addition, invention conjugates are more effective than unmodified pharmacologically active agents because cells and tissues contacted by the pharmacologically active agent(s) are protected from the potentially damaging effects of nitric oxide overproduction induced thereby as a result of the co-production of nitric oxide scavenger (e.g., dithiocarbamate), in addition to free pharmacologically active agent, when invention conjugate is cleaved.

21 Claims, 5 Drawing Sheets

OTHER PUBLICATIONS

Thomas et al., "The Hydrolysis Product of ICRF–187 Promotes Iron–Catalysed Hydroxyl Radical Production Via the Fenton Reaction," *Biochemical Pharmacology*, 45/10:1967–1972, 1993.

Wallace, "Nonsteroidal Anti–inflammatory Drugs and Gastroenteropathy: The Second Hundred Years," *Gastroenterology*, 112:1000–1016, 1997.

Wallace et al., "Tissue–Selective Inhibition of Prostaglandin in Rat by Tepoxalin: Anti–inflammatory Without Gastropathy?," *Gastroenterology*, 105:1630–1636, 1993.

Whittle et al., "Induction of nitric oxide synthase and microvascular injury in the rat jejunum provoked by indomethacin," *Br. J. Pharmacol*, 116:2286–2290, 1995.

* cited by examiner

CONJUGATES OF DITHIOCARBAMATES WITH PHARMACOLOGICALLY ACTIVE AGENTS AND USES THEREFOR

RELATED APPLICATIONS

This application is a continuation-in-part of PCT Application No. PCT/US98/10295, file May 19, 1998 which is a continuation of U.S. application Ser. No. 08/869,158, filed Jun. 4, 1997 now issued as U.S. Pat. No. 5,916,910, the entire contents of each of which is hereby incorporated by reference herein.

FIELD OF THE INVENTION

The present invention relates to novel conjugated forms of pharmacologically active agents, and methods for the preparation and use thereof. In a particular aspect of the invention, methods are provided for simultaneously treating a pathological condition with a pharmacologically active agent and reducing nitric oxide levels.

BACKGROUND OF THE INVENTION

Despite the advent of modem pharmaceutical technology, many drugs still possess untoward toxicities which often limit the therapeutic potential thereof. For example, although non-steroid anti-inflammatory drugs (NSAIDs) are a class of compounds which are widely used for the treatment of inflammation, pain and fever, NSAIDs (e.g., aspirin, ibuprofen and ketoprofen) can cause gastrointestinal ulcers, a side-effect that remains the major limitation to the use of NSAIDs (see, for example, J. L. Wallace, in Gastroenterol. 112:1000–1016 (1997); A. H. Soll et al., in Ann Intern Med. 114:307–319(1991); and J. Bjarnason et al., in Gastroenterol. 104:1832–1847 (1993)).

There are two major ulcerogenic effects of NSAIDs: (1) topical irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:65–70 (1985); and J. L. Carson, et al., in Arch. Intern. Med., 147:1054–1059 (1987)).

It is well recognized that aspirin and other NSAIDs exert their pharmacological effects through the inhibition of cyclooxygenase (COX) enzymes, thereby blocking prostaglandin synthesis (see, for example, J. R. Van in Nature, 231:232–235 (1971)). There are two types of COX enzymes, namely COX-1 and COX-2. COX-1 is expressed constitutively in many tissues, including the stomach, kidney, and platelets, whereas COX-2 is expressed only at the site of inflammation (see, for example, S. Kargan et al. in Gastroenterol., 111:445–454 (1996)). The prostagladins derived from COX-1 are responsible for many of the physiological effects, including maintenance of gastric mucosal integrity.

Many attempts have been made to develop NSAIDs that only inhibit COX-2, without impacting the activity of COX-1 (see, for example, J. A. Mitchell et al., in Proc. Natl. Acad. Sci. USA 90:11693–11697 (1993); and E. A. Meade et al., in J. Biol. Chem., 268:6610–6614 (1993)). There are at least two NSAIDs presently on the market (i.e., nabumetone and etodolac) that show marked selectivity for COX-2 (see, for example, E. A. Meade, supra.; and K. Glaser et al., in Eur. J. Pharmacol. 281:107–111 (1995)). These drugs appear to have reduced gastrointestinal toxicity relative to other NSAIDs on the market.

On the basis of encouraging clinical as well as experimental data, the development of highly selective COX-2 inhibitors appears to be a sound strategy to develop a new generation of anti-inflammatory drugs. However, the physiological functions of COX-1 and COX-2 are not always well defined. Thus, there is a possibility that prostagladins produced as a result of COX-1 expression may also contribute to inflammation, pain and fever. On the other hand, prostagladins produced by COX-2 have been shown to play important physiological functions, including the initiation and maintenance of labor and in the regulation of bone resorption (see, for example, D. M. Slater et al., in Am. J. Obstet. Gynecol., 172:77–82 (1995); and Y. Onoe et al., in J. Immunol. 156:758–764 (1996)), thus inhibition of this pathway may not always be beneficial. Considering these points, highly selective COX-2 inhibitors may produce additional side effects above and beyond those observed with standard NSAIDs, therefore such inhibitors may not be highly desirable.

Since anthracyclines such as adriamycin are commonly used antitumor agents, considerable efforts have also been made to develop strategies for reducing the acute and delayed cardiomyopathies induced by anthracyclines, while maintaining the therapeutic efficacy of these compounds. The molecular mechanism of cardiomyopathy is now attributed to the adriamycin-induced release of iron from intracellular iron proteins, resulting in the formation of an adriamycin-iron complex. The adriamycin-iron complex generates reactive oxygen species, causing the scission and condensation of DNA, peroxidation of phospholipid membranes, depletion of cellular reducing equivalents, interference with mitochondrial respiration, and disruption of cell calcium homeostasis (see, for example, Myers et al., in Science 197:165–167 (1977); and Gianni et al., in Rev. Biochem. Toxicol. 5:1–82 (1983)). In addition to cardiomyopathy, adriamycin administration causes cutaneous irritation and alopecia, mucositis (stomatitis and esophagitis), phlebosclerosis and hematologic toxicities and many other local and systemic toxicities.

Recently, ICRF-187 (i.e., dexrazoxane) has been demonstrated to be effective for the removal of iron from the anthracycline-iron complex, therefore preventing the cardiac toxicity in cancer patients receiving adriamycin chemotherapy (see, for example, Kolaric et al., in Oncology 52:251–5 (1995)). However, when chelated with iron, the iron-ICRF-187 complex per se is also very effective at promoting hydroxyl radical generation via the Fenton reaction, causing oxidative damage to tissues (see, for example, Thomas et al., in Biochem. Pharmacol., 45:1967–72 (1993)). In addition, since ICRF-187 is a strong chelator (having a structure similar to EDTA), it chelates not only low-molecular-weight iron, but also chelates iron from transferrin and ferritin, as well as copper from ceruloplasmin, thus potentially affecting normal cellular iron metabolism.

Accordingly, there is still a need in the art for modified forms of NSAIDs, and other pharmacologically active agents, which cause a reduced incidence of side-effects, relative to the incidence of side-effects caused by such pharmacologically active agents as aspirin, ibuprofen, and the like.

BRIEF DESCRIPTION OF THE INVENTION

In accordance with the present invention, there are provided conjugates of physiologically compatible nitric oxide scavengers (e.g., dithiocarbamates (DC)) and pharmacologically active agents (e.g., NSAIDS). Invention conjugates provide a new class of pharmacologically active agents (e.g., anti-inflammatory agents) which cause a much lower incidence of side-effects due to the protective effects imparted by modifying the pharmacologically active agents as described herein.

Recent evidence has shown that NSAID administration up-regulates the expression of inducible nitric oxide synthase (see, for example, B. J. R. Whittle et al., in Br. J. Pharmacol., 116:2286–2290 (1995)). Excessive nitric oxide produced from inducible nitric oxide synthase is known to contribute to the generation of mucosal damage (see, for example, S. J. Middleton et al., in Lancet 341:456–466 (1993); and M. J. S. Miller et al., in Scand. J. Gastroenterol., 264:11–16 (1993)). When chelated with iron (e.g., intracellular iron), nitric oxide scavengers (such as a dithiocarbamate-iron complex) becomes an effective nitric oxide scavenger which binds tightly to nitric oxide and reduces in vivo nitric oxide levels. It is now recognized that excessive nitric oxide production can induce the expression of COX-2, thereby enhancing the cascade of inflammatory reactions. Thus, scavenging NO by a nitric oxide scavenger (such as the dithiocarbamate-iron complex) could reduce the negative consequences brought about by excessive COX-2 levels, by reducing the expression of COX-2.

In summary, there are a number of advantages of conjugates according to the invention (e.g., DC-NSAID), including:

(i) reduced topical irritant effects of NSAIDs, (ii) enhanced tissue delivery of both drugs as a result of a decrease in net charges on the molecule, particularly for acidic NSAIDs such as aspirin, diclofenac and ibuprofen, thereby reducing the quantity of material which must be delivered to achieve an effective dosage, (iii) chelating intracellular free iron ions, thereby preventing iron-related oxidative damage, (iv) inhibiting VCAM-1 expression, thereby blocking neutrophil adherence to the vascular endothelium induced by NSAID administration, and (v) scavenging intracellular nitric oxide, thereby preventing the production of peroxynitrite, a potent oxidant, and reducing the induction of COX-2 expression, which could induce further inflammatory response.

In another aspect of the invention, there are described bio-cleavable conjugates of a suitable nitric oxide scavenger (e.g., dithiocarbamate) and an anti-neoplastic agent (e.g., adriamycin, wherein the resulting conjugate is referred to as DC-adriamycin), which alleviate some of the toxicities associated with administration of anti-neoplastics such as adriamycin. There are a number of advantages of DC-adriamycin over adriamycin alone, including:

(i) reducing cutaneous irritation and alopecia and vascular damage (because the conjugates are inactive until they have reached the intracellular site of action), (ii) chelating intracellular iron, thus reducing free radical-induced acute and delayed cardiomyopathies, and (iii) removing excessive nitric oxide produced from malignant and cancerous tissues.

DETAILED DESCRIPTION OF THE INVENTION

Figure 1:
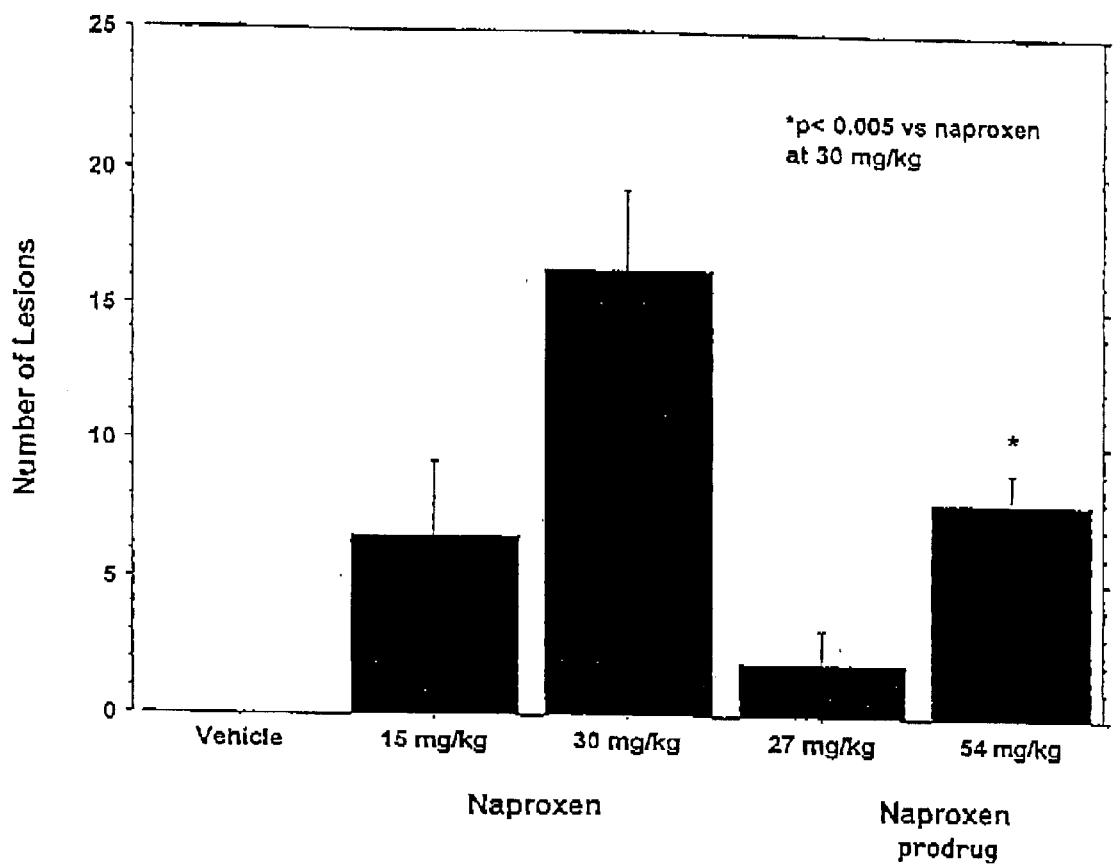
FIG. 1 illustrates the improved gastric safety of a Naproxen prodrug according to the invention (relative to unmodified Naproxen) in a rat model. The number of gastric lesions was measured three hours after oral dosing of fasted male Sprague-Dawley rats with vehicle, 2 different doses of naproxen or 2 different doses of a molar equivalent of Naproxen prodrug.

In accordance with the present invention, there are provided compounds comprising a suitable nitric oxide scavenger (e.g., a dithiocarbamate) covalently attached to a pharmacologically active agent.

As readily recognized by those of skill in the art, a variety of chemical entities can be used for scavenging nitric oxide, e.g., iron-chelating compounds such as dithiocarbamates, desferrioxamine (DF), ethylenediaminetetraacetic acid (EDTA), diethylenetriaminepentaacetic acid (DTPA), hydroxypyridinones, pyridoxalisonicotinoylhydrazone (PIH), quercetin, 1,2-dimethyl-3-hydroxpyrid-4-one (LI), phytic acid, dexrazoxane (ICRF-187), N,N-dibenzylethylene-diamine-N,N-diacetic acid (DBED), and the like.

Other nitric oxide scavenging compounds contemplated for use herein include: 2-mercaptonicotinic acid, nitronyl nitroxide, nitric oxide chelotropes (i.e., compounds contaning the 7,7,8,8-tetraalkyl-0-quinodimethane type moiety), dimercaptosuccinic acid, 2-phenyl-4,4,5,5-tetramethylimidazoline-1-oxyl 3-oxide (PTIO), carboxy-PTIO, phenyl-n-tert-butyl nitrone, and other nitrone derivatives, and the like.

Dithiocarbamates are sulfur-containing small molecules that are known heavy metal chelators (see, for example, F. W. Sunderman, in Ann. Clin. Lab. Sci., 8:259–69 (1978); and M. M. Jones and M. G. Cherian, in Toxicology, 62:1–25 (1990)). Dithiocarbamates such as diethyl-dithiocarbamate have been used clinically in the treatment of nickel poisoning (see, for example, Sunderman, supra) and were used in clinical trials for the treatment of AIDS patients (see, for example, E. Reisinger et al., in Lancet, 335:679 (1990)).

Dithiocarbamates such as pyrrolidine dithiocarbamate are potent inhibitors of nuclear factor kappa B in intact cells (see, for example, R. Schreck et al., in J. Exp. Med., 175:1181–1194 (1992)). In addition, nuclear factor kappa B has been shown to up-regulate the expression of cell adhesive molecules, including the vascular cell adhesive molecule I (VCAM-1; see, for example, M. F. Iademarco et al., in J. Biol. Chem., 267:16323–16329 (1992)). Endothelial expression of VCAM-1 causes the adherence of neutrophils to the endothelium, an early event leading to inflammation and subsequent vascular damage and reduction of blood flow (see, for example, M. N. Oppenheimer et al., in J. Immunol., 147:42207–4210 (1991)). It has been recognized that NSAID administration increases neutrophil adherence to the vascular endothelium in the gastric and mesenteric microcirculation (see, for example, J. L. Wallace et al., in Gastroenterol., 105:1630–1636 (1993); and H. Asako et al., in Am J. Physiol., 262:G903–G908 (1992)). Therefore, conjugates of NSAIDs with dithiocarbamate would block VCAM-1 expression, thereby avoiding the vascular problems associated with neutrophil adherence to the endothelium.

Suitable dithiocarbamate compounds contemplated for use in the practice of the present invention can be described with reference to generic structure I as follows:

   (1)

wherein:
each of $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or $R_1$ and $R_2$ cooperate to form a 5-, 6- or 7-membered ring including N, $R_1$ and $R_2$, or $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, x is 1 or 2, and M is a monovalent cation when x is 1, or M is a physiologically compatible divalent or trivalent transition metal cation when x is 2.

Presently preferred dithiocarbamate compounds having generic structure I are those wherein:
each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, or $R_1$ and $R_2$ cooperate to form a 5-, 6- or 7-membered ring including N, $R_1$ and $R_2$, and $M=Fe^{+2}$ or $Fe^{+3}$.

Especially preferred dithiocarbamate compounds having generic structure I are those wherein:
$R_1$ is selected from a $C_2$ up to $C_8$ alkyl or substituted alkyl, wherein the substituents are selected from carboxyl, acetyl, pyridinyl, pyrrolidinyl, amino, amido, hydroxy or nitro, and $R_2$ is selected from a $C_1$ up to $C_6$ alkyl or substituted alkyl, or $R_2$ cooperates with $R_1$ to form a 5-, 6- or 7-membered ring including N, $R_2$ and $R_1$, and $M=Fe^{+2}$.

The presently most preferred dithiocarbamate compounds having generic structure I are those wherein:
$R_1$ is selected from a $C_2$ up to $C_8$ alkyl or substituted alkyl, wherein the substituents are selected from carboxyl, acetyl, amido or hydroxy, and $R_2$ is selected from a $C_1$ up to $C_4$ alkyl or substituted alkyl, or $R_2$ cooperates with $R_1$ to form a 5- or 6-membered ring including N, $R_2$ and $R_1$, and $M=Fe^{+2}$.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)— and/or —N(R)-containing alkylene moieties, wherein R is hydrogen or a lower alkyl moiety. Presently preferred dithiocarbamates wherein $R_1$ and $R_2$ cooperate to form a ring structure include pyrrolidine dithiocarbamate, proline dithiocarbamate, pyridine dithiohcarbamate, pyridinium dithiocarbmate, pyrimidine dithiocarbamate, pyrroline dithiocarbamate, and the like.

Examples of presently preferred dithiocarbamates contemplated for use herein for the preparation of invention conjugates include sarcosine dithiocarbamate, iminodiacetic acid dithiocarbamate, diethyldithiocarbamate, diisopropyldithiocarbamate, sugar-linked dithiocarbamates (e.g., glucose-, lactose-, mannose-, fructose-linked dithiocarbamates, and the like), pyrrolidine dithiocarbamate, proline dithiocarbamate, and the like.

Monovalent cations contemplated for incorporation into the above-described dithiocarbamate compounds include $H^+$, $Na^+$, $NH_4^+$, tetraalkyl ammonium, and the like. Physiologically compatible divalent or trivalent transition metal cations contemplated for incorporation into the above-described dithiocarbamate compounds include charged forms of iron, cobalt, copper, manganese, ruthenium, or the like (e.g., $FE^{+2}$, $FE^{+3}$, $Co^{+2}$, $Co^{+3}$, $Cu^{+2}$, $Mn^{+2}$, $Mn^{+3}$ or $Ru^{+3}$). In accordance with invention, the ratio of dithiocarbamate-species to counter-ion M can vary widely. Thus, dithiocarbamate-containing nitric oxide scavenger can be administered without any added metallic counter-ion (i.e., $M=H^+$, or a transition metal cation to dithiocarbamate-species ratio of zero), with ratios of transition metal cation to dithiocarbamate-species up to about 1:2 (i.e., a 2:1 dithiocarbamate:transition metal cation complex) being suitable.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

Diseases and conditions contemplated for treatment in accordance with the present invention include inflammatory and infectious diseases, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., ulcerative colitis or Crohn s disease), diabetes, arthritis, asthma, Alzheimer s disease, Parkinson s disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation (e.g., liver inflammation, renal inflammation, and the like), burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDA, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington s disease, epilepsy, neurodegenerative disorders, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), ophthalmic diseases, post-angioplasty, restenosis, angina, coronary artery disease, and the like.

Pharmacologically active agents contemplated for modification in accordance with the present invention include:
NSAIDs, such as acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (Iodine), fenoprofen calcium (nalfon), flurobiprofen (ansaid), indomethacin (indocin, indometh, others), ketoprofen (orudis, oruvail), ketorolac tromethamine (toradol), magnesium salicylate (Doan s, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lomoxicam, nimesulide, indoprofen, remifenzone, salsalate, tiaprofenic acid, flosulide, and the like;
analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, and the like);

antidepressants (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimiprarnine maleate, protriptyline hydrochloride, and the like);

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate), antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antihypertensive drugs, such as diuretics (hydrochlorothiazide, chlorthalidone, metolazone, indapamide, furosemide, bumetanide, torsemide, triamterene, amiloride, spronolactone), beta-adrenergic blocking agents (acebutolol, atenolol, betaxolol, cartelol, labetalol, metoprolol, nadolol, penbutolol, pindolol, propranolol, timolol), angiotensin converting enzyme inhibitors (benazepril, captopril, enalapril, fosinopril, quinoapril, ramimpril, losartan), calcium channel- blocking agents (diltiazem, verapamil, amlodipine, felodipine, isradipine, nicardipine, nifedipine), aplha- adrenoceptor blocking agents, sympatholytics, and vasodilators (such as prazosin, terazosin, doxazosin, clonidine, guanabenz, guanfacine, methylodopa, guanethidine, guanethidine monosulfate, reserpine, hydralazine, minoxidil, and the like), as well as agents such as trimethaphan camsylate, phenoxybenzamine hydrochloride, pargyline hydrochloride, deserpidine, diazoxide, rescinnamine, sodium nitroprusside, rauwolfia serpentina, alseroxylon, phentolamine mesylate, and the like;

antihistamine/antipruritic drugs, such as ethanolamines (e.g., diphenhydramine, diphenhydramine hydrochloride, clemastine, clemastine fumarate, and the like), ethylenediamines (e.g., brompheniramine, brompheniramine maleate, chlorpheniramine, chlorpheniramine maleate, dexchlorpheniramine maleate, triprolidine, triprolidine hydrochloride, and the like), phenothiazines (e.g., promethazine), piperidines (e.g., hydroxzine, hydroxyzine hydrochloride, terfenadine, astemizole, azatadine, azatadine maleate, and the like), cyproheptadine, cyproheptadine hydrochloride, loratidine, carbinoxamine maleate, diphenylpyraline hydrochloride, phenindamine tartrate, tripelennamine hydrochloride, methdilazine hydrochloride, trimprazine tartrate, and the like;

immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., CHI-621 and dacliximab), buspirone, castanospermine, CD-59 (complement factor inhibitor), 5-lipoxygenase inhibitor (e.g., CMI-392), phosphatidic acid synthesis antagonists, ebselen, edelfosine, enlimomab, galaptin, platelet activating factor antagonists, selectin antagonists (e.g., ICAM4), interleukin-10 agonist, macrocylic lactone, methoxatone, mizoribine, OX-19, peptigen agents, PG-27, protein kinase C inhibitors, phosphodiesterase IV inhibitor, single chain antigen binding proteins, complement factor inhibitor, sialophorin, sirolimus, spirocyclic lactams, 5-hydroxytryptamine antagonist, anti-TCR monoclonal antibodies, CD5 gelonin and TOK-8801, and the like;

antimetabolite cytotoxics (azathioprine, cyclophosphamide), C5a release inhibitor, benzydamine, peldesine, pentostatin, SDZ-ASM-981, thalidomide, benzoporphyrin derivatives, arachidonate antagonists (e.g., halometasone, halobetasol propionate), corticosteriod (clobetasol propionate), growth hormone antagonists (octapeptide somatostatin analogue, lanreotide, angiopeptin and dermopeptin), thymopentin, and the like;

neuroprotective agents, such as α-adrenoreceptor antagonist (i.e, α-dihydroergocryptine), NMDA antagonists (e.g., 5,6,7-tichloro-THQTQ, remacemide, 2-piperazinecarboxylic acid, N-indologlycinamide derivatives, spiro[benzo(b)thiophen-4(5H) derivatives, CP-101606, eliprodil, dexanabinol, GV-150526, L-695902, L-701324, amantadine derivatives, dizocilpine, benzomorphan derivatives, aptiganel, (S)-α-phenyl-2-pyridine ethanamide dihyrochloride and 1-amino-cyclopentanecarboxylic acid), sodium channel antagonists (e.g., 619C89), glycine antagonists (e.g., glystasins), calcium channel antagonists (e.g., 3,5-pyridinedicarboxylic acid derivatives, conopeptides, 1-piperazineethanol, thieno[2,3-b]pyridine-5-carboxylic acid derivatives, NS-3034, nilvadipine, nisoldipine, tirilazad mesylate, 2H-1-enzopyran-6-ol, nitrone spin traps, iacidipine, iomeerzine hydrochloride, lemildipine, lifarizine, CPC-304, efonidipine, F-0401, piperazine derivatives), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives and 1-azulenesulfonic acid derivatives), brain-derived neurotropic factor, adrenergic transmitter uptake inhibitor (e.g., 1-butanamine), endothelin A receptor antagonists (e.g., benzenesulfonamide derivatives, GABA A receptor antagonists (e.g., triazolopyrimidine derivatives and cyclohexaneacetic acid derivatives), GPIIb IIIa receptor antagonists (e.g., C68-22), platelet aggregation antagonist (e.g., 2(1H)quinolinone derivatives, 1H-pyrrole-1-acetic acid derivatives and coumadin), Factor Xa inhibitor, CPC-211, corticotropin releasing factor agonist, thrombin inhibitor (e.g., cothrombins, fraxiparine, dermatan sulfate and heparinoid), dotarizine, intracellular calcium chelators (e.g., BAPTA derivatives), radical formation antagonists (EPC-K1,3-pyridinecarboxamide derivatives, superoxide dismutase, raxofelast, lubeluzole, 3H-pyrazol-3-one derivatives, kynurenic acid derivatives, homopiperazine derivatives, and polynitroxyl albumin), protein kinase inhibitors (e.g., 1H-1,4-diazepine), nerve growth agonist (e.g., floor plate factor-5), glutamate antagonist (e.g., cyclohexanepropanoic acid, riluzole, NS409 and acetamide derivatives), lipid peroxidase inhibitor (e.g., 2,5-cyclohexadiene-1,4-dione derivatives), sigma receptor agonist (e.g., cyclopropanemethanamine derivatives and SA-4503), thyrotropin releasing hormone agonist (e.g., JTP-2942, L-prolinamide and posatirelin), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline and benzonitrile derivatives), PARS inhibitors, Angiotensin I converting enzyme inhibitor (e.g., perindopril and ramipril), acetylcholine agonist (e.g., pramiracetam), protein systhesis antagonist (e.g., procysteine), phosphodiesterase inhibitor (e.g., propentofylline), opioid kappa receptor agonist (e.g., 10H-phenothiazine-2-carboxamine derivatives), complement factor inhibitor (sCRI fragments), somatomedin-1, carnitine acetyltransferase stimulant (e.g., acetylcarnitine), and the like;

T cell inhibitors such as synthetic leucocyte antigen derived peptides, interleukin-1 receptor antagonist, MG/AnergiX, anti-CD3 monoclonal antibodies, anti-CD23 monoclonal antibodies, anti-CD28 antibodies, anti-CD2 monoclonal antibodies, CD4 antagonists, anti-E selectin antibodies, MHC inhibitors, monogens, mycophenolate mofetil, LRA-1 inhibitors, selectin inhibitors, and the like;

antimigraine agents, such as MK-462, 324C91, Phytomedicine, (S)-fluoxetine, calcium channel antagonists (e.g., nimodipine/Nimotop, flunarizine, dotarizine/FI-6026, iomerizine HCL/KB-2796, CPC-304, and CPC-317), α-dihydroergocryptine, 5-HT1 agonists, (e.g., Sumatriptan/limitrex, Imigran, GR-85548, 311C, and GR-127607), 5-HT1D agonists, 5-HT1A antagonists, 5-HT1B antagonists (e.g., CP-93129), 5-HT1D antagonists (e.g., 1H-indole-5-ethanesulfonamide derivatvies and 1H-indole-5-methanesulfonamide), 5-HT1D receptor cloned (e.g., 5-HT1D agents), 2-thiophenecarboxamide, 3-piperidinamine, diclofenac potassium, dihydroergotamine (e.g., DHE 45®), ergotamine tartrate, dolasetron mesilate, dotarizine, flupirtine, histamine-H3 receptor agonist, indobufen, 1-azulenesulfonic acid derivatives, (e.g., S-9977), bradykinin antagonists, nitric oxide reductase inhibitors (e.g., BN-52296), nitric oxide receptor antagonists, substance P antagonists (e.g., Capsaicin/Nasocap), endopeptidase inhibitors (e.g., neutral endopeptidase, cloned), piperazine derivatives, neurokinin 1 antagonists, metergoline, dopamine D2 antagonist (e.g., metoclopramide+lysine acetyl), enkephalinase inhibitors (e.g., neutral endopeptidase), 5-HT2 antagonists (e.g., LY-053857), 5-HT3 antagonists (e.g., Dolasetron mesilate/MDL-73147, and 4H-carbazol4-one derivatives), tenosal, tolfenamic acid, cyclooxygenase inhibitors (e.g., carbasalate/carbaspirin calcium, and tenosal/MR-Y134), alpha adrenoreceptor antagonists (e.g., arotinolol, and dihydroergocryptine), opioid agonists (e.g., flupirtine/D-9998), beta adrenergic antagonists (e.g., propranolol), valproate semisodium, propanolol hydrochloride, isomethepene mucate, dichloralphenazone, and the like;

antiarthritic agents, such as anti-CD4 monoclonal antibodies, phospholipase A1 inhibitor, loteprednol, tobramycin, combinations of loteprednol and tobramycin, salnacedin, amiprilose, anakinra, anergiX, anti-B7 antibody, anti-CD3H, anti-gp39, anti-MHC MAbs, anti-rheumatic peptides, anti-Tac(Fv)-PE40, AP-1 inhibitors, AR-324, purine nucleotide phosphorylase inhibitors (e.g., BCX-5), bindarit, CD2 antagonist (e.g., BTI-322), campath-1H, CD4 antagonist (e.g., CE9.1 and SB-210396), tumor necrosis factor antagonist (e.g., p80 TNFR, rhTNFbp, peptide T, CenTNF, thalidomide, CDP-571 and TBP-1), cobra venom factor, interleukin 1a agonist (e.g., cytogenin), interleukin 2 receptor antagonist (e.g., dacliximab), ICAM 1 antagonist (e.g., enlimomab), interleukin 1 beta converting enzyme inhibitors (e.g., ICE-inhibitors), interferons (e.g., thymocartin), interleukin-10, interleukin-13, interleukin 1 antagonist (e.g., SR-31747 and TJ-114), interleukin-2 antagonist (e.g., sirolimus), phospholipase C inhibitor, neurokinin 1 antagonist (e.g., L-733060), laflunimus, leflunomide, leucotriene antagonists, levamisole, LFA3TIP, macrocyclic lactone, MHC class II inhibitors, mizoribine, mycophenolate mofetil, NfkB inhibitors, oncolysin CD6, peldesine, pidotimod, PKC-RACK inhibitors, PNP inhibitors, reumacon, CD28 antagonist, roquinimex, RWJ-50271, subreum, T7 vector, tacrolimus, VLA antagonist (e.g., TBC-772), transforming growth factor beta agonist, methionine synthase inhibitors (e.g., vitamin B12 antagonist), adenosine A2 receptor agonist (e.g., YT-146), CD5 antagonist (e.g., zolimomab), 5-lipoxygenase inhibitor (e.g., zileuton, tenidap, and ABT-761), cyclooxygenase inhibitor (e.g., tenoxicam, talmetacin, piroxicam, piroxicam cinnamate, oxaprozin, NXTHIO, ML-3000, mofezolac, nabumetone, flurbiprofen, aceclofenac, diclofenac, and dexibuprofen), metalloproteinase inhibitor (e.g., XR-168, TNF convertase inhibitors, GI-155704A, AG-3340 and BB-2983), nitric oxide synthase inhbitors (i.e, ARL-16556), phospholipase A2 inhibitor (e.g., ARL-67974), selectin antagonist (e.g., CAM inhibitors), leucotriene B4 antagonist (e.g., CGS-25019C), collagenase inhibitor (e.g., GR-129574A), cyclooxygenase 2 inhibitor (e.g., meloxicarn), thromboxane synthase inhibitor (e.g., curcumin), cysteine protease inhibitor (e.g., GR-373), metalloproteinase inhibitor (D-5410), lipocortins synthesis agonist (e.g., rimexolone, predonisolone 21-farnesylate, HYC-141, and deflazacort), chelating agent (diacerein), elastase inhibitors, DNA directed RNA polymerase inhibitor (e.g., estrogens), oxygen radical formation antagonist (e.g., glucosamine sulfate), thrombin inhibitors (e.g., GS-522), collagen inhibitors (e.g., halofuguinone), hyaluronic acid agonist (e.g., NRD-101, hylan, Dispasan, and Hyalart), nitric oxide antagonists (e.g., hydroxocobalamin), stromelysin inhibitors.(e.g., L-758354), prostaglandin E1 agonist (e.g., misoprostol, and misoprostol+diclofenac), dihydrofolate reductase inhibitor (e.g., trimetrexate, and MX-68), opioid antagonist (e.g., nalmefene), corticotropin releasing factor antagonist (e.g., NBI-103, and NBI-104), proteolytic enzyme inhibitor (e.g., protease nexin-1, and NCY-2010), bradykinin antagonist (e.g., tachykinin antagonists, and NPC-17731), growth hormone antagonist (e.g., octreotide), phosphodiesterase IV inhibitor (e.g., PDEIV inhibitors), gelatinase inhibitor (e.g., REGA-3G12), free radical scavengers (e.g., SIDR-1026), prostaglandin synthase inhibitors (e.g., sulfasalazine), phenylbutazone, penicillamine, salsalate, azathioprine, indomethacin, meclofenamate sodium, gold sodium thiomalate, ketoprofen, auranofin, aurothioglucose, tolmetin sodium, and the like;

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antifungal agents (e.g., griseofulvin, keloconazole, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

antioxidants (e.g., N-acetylcsysteine, Vitamin A, Vitamin C, Vitamin E, β carotene, EUK-8, flavonoids, glutathione, α-lipoic acid, melatonin, retinols, and the like);

anti-infectives (e.g., miconazole, vidarabine, inosine, pranobex, vidarabine, inosine prabonex, cefpimizole sodium), fradiomycin, and the like);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically active protein, including the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

septic shock agents, such as angiogenesis inhibitors (OLX-514), bradykinin antagonists (e.g., CP-0502, and NPC-17731), complement factor inhibitors (e.g., C3 convertase inhibitor), C5a release inhibitors (e.g., CAB-2.1), dopamine agonists (e.g., dopexamine), elastase inhibitors (e.g., ONO-5046), E selectin antagonists (e.g., CY-1787), farnesyltransferase inhibitors (RBE limonene), immunostimulants (e.g., CGP-19835A, lipid A vaccine, edobacomab, nebacumab, StaphGAM, and diabodies), immunosuppressants (e.g., CytoTAB, and transcyclopentanyl purine analogues), interleukin 1 antagonists (e.g., interleukin 1 receptors), interleukin 1 receptor antagonists (e.g., anakinra), interleukin 1b antagonists (e.g., interleukin-1β), interleukin 1 beta converting enzyme inhibitors (e.g., ICE-inhibitors), interleukin 8 antagonists (e.g., IL-8 receptor), interleukin 13 agonists (e.g., intereleukin-13), ITF-1697, lipase clearing factor inhibitors (e.g., SC-59735), membrane permeability enhancers (e.g., Bactericidal Permeability Increasing protein/BPI), nitric oxide antagonists (e.g., hydroxocobalamin), nitric oxide synthase inhibitors (e.g., L-NMMA, and α-methyl-N-delta-iminoethyl-ornithine), P2 receptor stimulants (e.g., ATP analogues), phosphatidic acid synthesis antagonists (e.g., lisofylline), phospholipase A2 inhibitors (e.g., S-448, acylpyrrole-alkanoic acid derivatives, and indoleacetic acid derivatives), platelet activating factor antagonists (e.g., ABT-299, TCV-309, SM-12502, (2RS,4R)-3-(2-(3-pyridinyl)-thiazolidin-4-oyl)indoles, UR-12670, and E-5880), prostacyclin agonists (e.g., taproots), prostaglandin E1 agonists (e.g., TLC C-53), protein kinase inhibitors (e.g., SB-203580), protein kinase C inhibitors, protein synthesis antagonists (e.g., procysteine), proteolytic enzyme inhibitors (e.g., nafamostat), SDZ-PMX-622, selectin antagonists (e.g., sulfated glycolipid cell adhesion inhibitors), thrombin inhibitors (e.g., GS-522), TNF receptor-Ig, tumor necrosis factor antagonists (e.g., anti-TNF MAbs, MAK-195F, TBP-I, Yeda, rhTNFbp, and CDP-571), tumor necrosis factor alpha antagonists (e.g., E-5531), and the like;

multiple sclerosis agents, such as 4-aminopyridine, 15±deoxyspergualin, ACTH, amantadine, antibody adjuvants (e.g., poly-ICLC, and poly-IC+poly-L-lysine+carboxymethylcellulose), anti-cytokine MAb (CDP-835), anti-inflammatory (e.g., CY-1787, and CY-1503), anti-selectin MAb (e.g., CY-1787), anti-TCR MAb (e.g., NBI-114, NBI-115, and NBI-116), bacloten, bethanechol chloride, carbamazepine, carbohydrate drugs (e.g., CY-1503), clonazepam, CNS and immune system function modulators (e.g., NBI-106, and NBI-107), cyclophosphamide, cyclosporine A, cytokines (e.g., IFN-α, Ifaferone, IFN-β 1b, betaseron, TGF-β2, PEG-TGF-β2, betakine, IFN-β/Rebif, frone, interferon-β, and IFN-β), CD4+T cell inhibitors (e.g., AnergiX), CD28 antagonists (e.g., B7-1, B7-2, and CD28), directcytotoxicity therapies (e.g., benzoporphyrin derivative (BPD)), FK-506, growth factors (e.g., glial growth factor, GGF, nerve growth factors, TGF-β2, PEG-TGF-β2, and betakine), humanized MAb (e.g., anti-IFN-γMAb, smart anti-IFN-γMAb, anti-Tac antibody, and smart anti-Tac antibody), humanized anti-CD4 MAb (e.g., anti-CD4 MAb, centara), hydrolase stimulants (e.g., castanospermine), IFN-α, IFN-γ antagonist (e.g., anti-IFN-γ MAb, and smart anti-IFN-γ MAb), IL-2 antagonists (e.g., tacrolimus, FK-506, FR-900506, Fujimycin, Prograf, IL-2 fusion toxin, and DAB$_{389}$IL-2), IL-4 antagonists (e.g., IL4 fusion toxin, and DAB$_{389}$IL4), immune-mediated neuronal damage inhibitors (e.g., NBI-114, NBI-115, and NBI-116), immunoglobins, immunostimulants (e.g., poly-ICLC, edelfosine, ALP, ET-18-OCH3, ET-18-OME, NSC-24, and poly-IC+poly-L-lysine+carboxymethyl-cellulose), immunosuppressants (e.g., azathioprine, AI-100 animal protein, rDNA human protein AI-101, peptide, AI-102, castanospermine, tacrolimus, FK-506, FR-900506, Fujimycin, Prograf, anti-leukointegrin MAb, Hu23F2G, primatized anti-CD4 antibody, CE9.1, Galaptin 14-1, GL14-1, Lectin-1, recombinant IML-1, linomide, roquinimex, LS-2616, transcyclo-pentanyl purine analogs, MS-6044, spanidin, 15-deoxyspergualin, deoxyspurgiline, gusperimus HCL, NSC-356894, NKT-01, TCR, CD3/Ti, cyclosporine, OL-27-400, SandImmune, Human IL-10, monogens, anti-TCR MAbs, TCAR MAbs, Monogen TM 19, Monogen TM27, Monogen TM29, Monogen TM31, peptigen TP12, anti-CD4 MAb, cantara, immunophilins, VX-10367, VX-10393, VX-10428, synthetic basic copolymer of amino acids, copolymer-1, COP-1, T lymphocyte immunofuision (TIF) protein, and cyclophosphamide), integrin antagonists (e.g., anti-integrin (cell adhesion molecule α4β1 integrin) MAbs, AN-100225, and AN-100226), interferon agonists (e.g., poly-ICLC, and poly-IC+poly-L-lysine+carboxymethyl-cellulose), interferon-β-1b, isoprinosine, IV methylprednisolone, macrolides (e.g., tacrolimus, FK-506, FR-900506, Fujimycin, and Prograf), MAO B inhibitors (e.g., selegiline, and Parkinyl), methotrexate, mitoxantrone, muscle relaxants (e.g., RGH-5002), muscarinic antagonists (e.g., RGH-5002), neurosteroids (e.g., NBI-106, and NBI-107), octapeptides (e.g., peptide T), oxybutinin chloride, oxygen free radical antagonists (e.g., tetrandrine, biobenzyl-isoquinoline alkaloid), peptide agonists (e.g., peptide T), phenoxybenzamine, phospholipase C inhibitors (e.g., edelfosine, ALP, ET-18-OCH3, ET-18-OME, NSC-24), photodynamic therapies (e.g., benzoporphyrin derivative (BPD)), plasmapheresis, platelet activating factor antagonists (e.g., ginkgolide B, and BN-52021), potassium channel antagonists (e.g., aminodiaquine, and EL-970), propranolol, prostaglandin synthase inhibitors (e.g., sulfasalazine, salazosulfa-pyridine, PJ-306, SI-88, azulfidine, salazopyrin), protease antagonists (e.g., ginkgolide B, and BN-52021), recombinant soluble IL-1 receptors, spergualin analogs (e.g., spanidin, 15-deoxyspergualin, deoxyspurgiline, gusperimus HCl, NSC-356894, NKT-01), TCR peptide decoys (e.g., NBI-114, NBI-115, and NBI-116), TCR peptidomimetic decoys (e.g., NBI-114, NBI-115, and NBI-116), TCR peptide vaccines (e.g., AI-208 (Vβ6.2/6.5 phenotype)), selectin antagonists (e.g., lectin-1, and recombinant IML-1), soluble TNF receptor I, TCARs (e.g., TCR, CD3/Ti, and peptigen TP12), TNF antagonists (e.g., thalidomide, and TNF inhibitors), tricyclic antidepressants, and the like;

organ transplantation agents, such as anti-CD25 MAbs, anti-Tac antibodies, anti-TNF MAb (e.g., CDP571), apoptosin, azathioprines (e.g., imuran), BCX-34, CA3, CD28, complement inhibiting factors (e.g., CD59), CTLA4Ig, cyclosporines (e.g., CsA), FK-506/rapamycin binding proteins (FKBP), glucocorticoids, humanized version of OKT3 (e.g., huOKT3-185), mycophenolate mofetil, hydroorotate dehydrogenase inhibitors (e.g., Brequinar), orthoclone OKT3 (e.g., IgG2a anti-T cell murine monoclonal antibody, and muromonab-CD3), rapamycins (e.g., AY-22989), and streptomyces isolates (e.g., FR-900520, and FR-900523), and the like;

systemic lupus erythematosus (SLE) agents, such as androgen-derived steriods (e.g., Org-4094), anti-CD4 humanized antibodies, anti-DNA/V-88, anti-idiotypic murine MAb (e.g., anti-idiotypic antibody to 3E10/MAb1C7), CD2 antagonists (e.g., CD2), complement inhibitors (e.g., recombinant MCP-based complement inhibitors), cyclosporines (e.g., Sandimmune, cyclosporine analog, OG-37325, cyclosporin-G, and NVal-CyA), cytokines (e.g., IL-4 fusion toxin), cytokine receptor antagonists (e.g., immunomodulatory cytokines), E-selectin antagonists (e.g., anti-ELAM, and CY-1787), FK506/tacrolimus (e.g., Prograf), hypercalcemic agents (e.g., KH-1060), IFN-γ antagonists (e.g., anti-IFN-γ

MAb, and smart anti-IFN-γ MAb), IL-1β converting enzyme inhibitors (ICE), IL-2 produced by *E. coli* (e.g., celmoleukin, IL-2, TGP-3, and Celeuk), immunoglobulins (e.g., anti-ELAM, CY-1788, and humanized CY-1787), immunostimulants (e.g., thymotrinan, RGH-0205, and TP3), immunosuppressants (e.g., Rapamycin, AY-22989, NSC-226080, NSC-606698, anti-CD4, T-cell inhibitor, anti-tac MAb, smart anti-tac MAb, Migis (membrane immunoglobulin-isotope specific) antibodies, SM-8849, immunophilins, VX-10367, VX-10393, VX-10428, mycophenolate mofetil, ME-MPA, RS-61444, cyclosporine, OL-27-400, Sandimmune, IL-4 fusion toxin, trypanosomal inhibitory factor (TIF), T-cell receptor, CD3/Ti, Org-4094, anti-TBM, CP 17193, Leflunomide/A-77-1726, ELAM-1, AnergiX, Spanidin, 15-deoxyspergualin, deoxyspurgiline, gusperimus hydrochloride, NSC-356894, NKT-01, Roquinimex, LS-2616, linomide, LJP-394, and CD-59 antigen), immunotoxins (e.g., Zolimomab aritox, xmmly-h65-rta, xomazyme-lym/CD5-Plus, OrthoZyme-CD5+, XomaZyme-H65-rta, Xomazyme-CD5 Plus), intravenous immunoglobulins (e.g., IVIG), integrin antagonists (e.g., integrin blockers), Migis antibodies, monoclonal antibody therapeutics, murine MAb (e.g., anti-SLE vaccine, and MAb 3E10), primatized anti-CD4 antibodies (e.g., CE9.1), protease inhibitors (e.g., matrix metalloprotease (MMP) inhibitors, and stromelysin), protein synthesis antagonists (e.g., anti-CD6-bR, anti-T12-bR, and oncolysin CD6), purine nucleoside phosphorylase inhibitors (e.g., BCX-25, and BCX-14), selectin antagonists (e.g., CY1503, and Cylexin), spergualin analogues (e.g., Spanidin, 15-deoxyspergualin, deoxyspurgiline, gusperimus hydrochloride, NSC-356894, and NKT-01), T cell inhibitors (e.g., AnergiX), tumor necrosis factor (TNF) antagonists, and the like;

Alzheimer's disease agents, such as ACh release enhancers (e.g., T-588 (benzothiophene derivative)), acetylcholine release stimulants (e.g., DUP-996 and analogues), AMPA agonists (e.g., AMAlex, and Isoxazole compound series), AMPA GluR agonist (e.g., IDRA-21[7-chloro-3-methyl-3,4-dihydro-2H-1,2,4-benzothiadiazinine]), AMPA GluR antagonists (e.g., S-18986, and related quinolone derivatives), anticholinesterases (e.g., E-2020), Ca-antagonists (e.g., NS-649, spider venom-derived ICM peptides and analogues, and substituted 2-aminoindanes compound series), combined anticholinesterase and muscarinic AChR antagonists (e.g., PD142676), K-channel blockers (e.g., Trans-R4-(4-methoxyphenyl-methyl) cyclohexylanine and analogues, and margatoxin-based functional and/or structural analogues), MI muscarinic receptor agonists (e.g., Xanomeline), NMDA antagonists (e.g., certain indole derivatives, and $(R-(R^1,S^1))-\alpha-(4-$hydroxyphenyl)-beta-methyl-4-(phenylmenthyl)-1-piperidinepropanol and analogues), nicotinic AChR agonists (e.g., ABT-418 [isoxazole, 3-meth-5-(1-meth-2-pyrrolidinyl)]), and the like;

antiparkinson agents (e.g., ethosuximide, and the like);

psoriasis agents, such as 5-LO inhibitors (e.g., Wy-50295, Wy-49232, Lonapalene, RS-43179, MK-886, L-663536, ETH-615, DUP-654, Zileuton, epocarbazolin-A, and A-64077), 5-LO/CO inhibitors (e.g., BF-397, Tenidap, CP-309, and CP-66248), angiogenesis inhibitors (e.g., platelet factor 4), anticancer antibiotic (e.g., AGM-1470, and TNP-470), anti-inflammatory cytochrome P450 oxidoreductase inhibitors (e.g., DuP-630, and DuP-983), antiproliferative compounds (e.g., Zyn-Linker), arachidonic acid analogues (e.g., CD581, and CD554), arachidonic acid antagonists (e.g., Lonapalene, RS-43179, triamcinolone acetonide with penetration enhancer Azone, betamethasone dipropionate steroid wipe, G-202, Halobetasol propionate, ultravate, Halometasone, C-48401-Ba, and Sicorten), beta-glucan receptor antagonists, betamethasone steroid wipes, calcium metabolic moderators (e.g., Tacalcitol, Bonealfa, TV-02 ointment, Ro-23-6474, KH-1060, Calcipotriol, BMS-181161, BMY-30434, Dovonex, and Divonex), CD4 binding inhibitors (e.g., PIC 060), cell adhesion compounds (e.g., CY-726, VCAM-1, ELAM-1, and ICAM), cell adhesion inhibitors (e.g., selectin inhibitor, GM-1930), cellular aging inhibitors (e.g., Factor X), corticosteroids (e.g., Halobetasol propionate, ultravate, Halometasone, C-48401-Ba, and Sicorten), cyclosporin analogues (e.g., IMM-125), dihydrofolate reductase inhibitors (e.g., G-301, dichlorobenzoprim, methotrexate, and methotrexate in microsponge delivery system), E-selectin inhibitors (e.g., ISIS 4730), endogenous active form of vitamin $D_3$ (e.g., Calcitriol, and Du-026325), fibroblast growth factor antagonists (e.g., Saporin mitotoxin, and Steno-Stat), fumagillin analogues (e.g., AGM-1470, and TNP-470), G-proteins and signal transduction compounds (e.g., CPC-A), gel formulations for acne (e.g., nicotinamide, N-547, and Papulex), growth hormone antagonists (e.g., Octreotide, Sandostatin, Lanreotide, angiopeptin, BIM-23014, and Somatuline), humanized antibodies (e.g., anti-CD4 antibody), hydroorotate dehydrogenase inhibitors (e.g., Brequinar sodium, bipenquinate, and DuP-785), ICAM-1 inhibitors (e.g., ISIS 939), IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, and FK-506), IL-2 receptor-targeted fusion toxins (DAB3891L-2), IL-8 receptors, immunostimulants (e.g., Thymopentin, and Timunox), immunosuppressants (e.g., XomaZyme-CD5 Plus, cyclosporine, Sandimmune, SR-31747, anti-CD11, 18 MAb, Tacrolimus, Prograf, FK-506, and FK-507), immunosuppressive agents targeting FK506 (e.g., immunophilins, VX-10367, and VX-10428), immunotoxins MAb directed against CD antigen (e.g., XomaZyme-CD5 Plus), leukotriene antagonists (e.g., Sch-40120, Wy-50295, and Wy-49232), leukotriene B4 antagonists (e.g., SC41930, SC-50605, SC-48928, ONO-4057, LB-457, LY-255283, LY-177455, LY-223982, LY-223980, and LY-255253), leukotriene synthesis inhibitors (MK-886, and L-663536), lipase clearing factor inhibitors (e.g., 1-docosanol, and lidakol), lipid encapsulated reducing agent (e.g., Dithranol), liposomal gel (e.g., Dithranol), LO inhibitors (e.g., CD581, CD554, Masoprocol, and Actinex), lithium succinate ointments (e.g., lithium salts, and Efalith), LO/CO inhibitors (e.g., P-8892, P-8977, CHX-108, and FPL-62064), membrane integrity agonists (e.g., lithium salts, and Efalith), microtubule inhibitors (e.g., Posophyliotoxin-containing compound, and Psorex), octapeptide somatostatin analogues (e.g., Lanreotide, angiopeptin, BIM-23014, and Somatuline), oligonucleotides (e.g., ISIS 4730, ISIS 3801, ISIS 1939, and IL-1 inhibitors), peptide agonists (e.g., octapeptide, and peptide T), PKC inhibitors, phospholipase A2 compounds, pospholipase D compounds, photodynarnic anticancer agents (e.g., 5-aminolevulinic acid, and 5-ALA), photodynamic therapies (e.g., benzoporphyrin derivative, synthetic chlorins, synthetic porphyrins, and EF-9), photosensitizer (e.g., Porfirmer sodium), PKC inhibitors (e.g., Safingol, and Kynac), platelet activating factor antagonists (e.g., TCV-309), platelet aggregation inhibitors (e.g., CPC-A), prodrug NSAIDs (e.g., G-201), prostaglandin agonist (e.g., eicosapentaenoic acid+gamma-linolenic acid combination, and Efamol Marine), protein inhibitors (e.g., SPC-103600, and SPC-101210), protein kinase C (PKC) inhibitors (e.g., Ro-31-7549, Ro-31-8161, and Ro-31-8220), protein synthesis antagonists (e.g., Calcitriol, Du-026325, LG-1069, LG-1064, AGN-190168, Namirotene, and CBS-211A), purine nucleoside phosphorylase inhibitors (e.g., BCX-34), radical formation agonists (e.g., benzoporphyrin derivative), recombinant antileukoproteinases (e.g., ALP-242), retinoids (e.g., BMY-30123, LG-1069, and LG-1064), retinoid derivatives (e.g., AGN-190168), rapamycin binding proteins (FKBP) (e.g., immunophilins, VX-10367, and VX-10428), second generation monoaromatic retinoids (e.g., Acitretin, and Neotigason), soluble IL-1, IL-4 and IL-7 receptors, somatostatin and somatostatin analogues (e.g., Octreotide, and Sandostatin), steroids, (e.g., AGN-191743), streptomyces anulatus isolates (e.g., epocarbazolin-A), superoxide dismutase (e.g., EC-SOD-B), thymidylate synthase inhibitors (e.g., AG-85, MPI-5002, 5-FU in biodegradable gel-like matrix, 5-FU and epinephrine in biodegradable gel-like matrix, and AccuSite), topical formulations (e.g., P-0751, and P-0802), transglutaminase inhibitors, tyrphostin EGF receptor kinase blockers (e.g., AG-18, and AG-555), VCAM-1 inhibitors (e.g., ISIS 3801), vitamin D analogues (e.g., Ro-23-6474, KH-1060, Calcipotriol, BMS-181161, BMY-30434, Dovonex, and Divonex), vitamin $D_3$ analogues (e.g., Tacalcitol, Bonealfa, TV-02 ointment), and vitamin $D_3$ derivatives (e.g., 1,2-diOH-vitamin $D_3$), and the like;

diabetes agents, such as ACE inhibitors (e.g., captopril), amylin, amylin agonists and antagonists (e.g., Normylin™, AC137, GC747, AC253, and AC625), autoimmune compounds (e.g., AI-401), capsaicins (e.g., Zostrix-HP), cell regulators (e.g., protein kinase C inhibitors, and Balanol), domperidones (e.g., Motilium®), fluvastatins (e.g., Lescol), FOX 988, fusion toxins (e.g., $DAB_{389}IL-2$, and $DAB_{486}IL-2$), gene therapies (e.g., Transkaryotic Therapies), glucagons (e.g., recombinant yeast glucagon), IL-10 compounds, iloprost, immunosuppressives (e.g., tacrolimus, Prograf, and FK-506), proinsulin, insulin and insulin analogues (e.g., AI-401, Nu-Insulin compounds, Humulin, Iletin, Humalog™, LYs-Pro, and Amaryl), insulin-like growth factors (e.g., Chiron/Ciba-Geigy compounds, Fujisawa compounds, and Genetech compounds), insulinotropins (e.g., Pfizer/Scios Nova compounds), nerve growth factors (e.g., Genentech compounds), oral hypoglycemics (e.g., AS-6, glimepiride, Amaryl, CL 316,243, acarbose, miglitol, recombinant yeast glucagon, GlucaGen™, NovoNorm™, glipizide, insulinotropin, and CI-991/CS-045), platelet-derived growth factors (e.g., Zymo Genetics/Novo Nordisk compounds), sulfonylureas (e.g., tolbutamide, acetohexamide, tolazamide, and chlorpropramide), T cell approaches (e.g., anergize, AnergiX™, Procept compounds, and T cell Sciences compounds), and tolrestats (e.g., Alredase®, and ARI-509), activin, somatostatin, and the like;

stroke agents, such as 5-HT antagonists (e.g., Piperazine derivative), 5-HT reuptake inhibitors (e.g., Milnacipran, and Dalcipran), 5-HT 1A agonists (e.g., SR-57746A, and SR-57746), 5-HT 3 agonists (e.g., SR-57227), 5-HT 4 antagonists, 5-lipoxygenase inhibitors (e.g., low MW dual 5-lipoxygenase and PAF inhibitor CMI-392), ACh agonists (e.g., Pramiracetam, Choline-L-alfoscerate, L-alpha-glycerylphosphoryl-choline, and Delecit), adenosine agonists (e.g., GP-1-4683, ARA-100, and arasine analogs), adenosine A1 receptor agonists (e.g., Azaisotere, 2-chloro-N-[4 (phenylthio)-1-piperidinyl]adenosine, and 2120136), adenosine reuptake inhibitors (e.g., Diphenyloxazole derivatives), adrenergic transmitter re-uptake inhibitors (e.g., Bifemelane, E-0687, MCI-2016, Alnert, and Celeport), aldose reductase inhibitors (e.g., Spiro-3' pyrroline derivatives), alpha antagonists (e.g., Drotaverine acephyllinate, and Depogen), alpha 2 agonists (e.g., SNAP-5083, SNAP-5608, and SNAP-5682), AMPA receptor agonists (e.g., heterocyclic compound SYM-1207, and heterocyclic compound SYM-1252), AMPA receptor antagonists (e.g., LY-293558, and LY-215490), Ancrod/Arvin, aspirin, benzothiazoles (e.g., Lubeluzole, and R87926), benzodiazepine receptor antagonists (e.g., 3-oxadiazolyl-1,6-naph-thyridine derivatives, Tetracyclic imidazodiazepineseries imidazenil, FID-02-023, and Ro-23-1412), blood substitutes, bradykinin antagonists (e.g., CP-0127, Bradycor, and Septicor), C5a release inhibitors (e.g., protein derivative CMI46000), calcium antagonists (e.g., Lemildipine, NB-818, NPK-1886, Trimetazidine derivative, lomerizine KP-2796, Diltiazem analog clentiazem maleate, and TA-3090), calcium channel antagonists (e.g., nitrendipine-like compound diperdipine, YS-201, U-92032, Diltiazem derivative, 1058, SM-6586, KP-840, F-0401, D-31-D, Tetrahydronaphthalene derivatives, fasudil, AT-877, H-7, HA-1044, HA-1077, Eril, darodipine, dazodipine, PY-108-068, Plimo, Dihydropy-ridine, AE 0047, GJ-0956, Lacidipine, GR-43659, GR-43659X, GX-1048, S-312-d, S-312, S-830312, Nilvadipine, and FK-235), calpain inhibitors (e.g., AK-275, and CX-275), camitine palmitoyl-transferase inhibitors, carvedilol, cerebral calcium antagonist vasodilators (e.g., Nimodipine, and Nimotop), cholinesterase inhibitors (e.g., indole and indazole derivatives, and Tacrine analog), complement factor inhibitors (e.g., TK9C, protein derivative TP16, compinact A, compinact C, Factor D inhibitors, and soluble, recombinant MCP-based complement inhibitors), complement inhibitors (e.g., sCRI/BRL-55730, and YM-203), coronary vasodilators (e.g., Nicorandil, RP46417, SG-75, and Adancor), CPC-111, cytidyl diphosphocholine/citicholines, cytokines (e.g., NBI-117), Dexanabiol, dopamine agonists, EAA receptors, endothelin antagonists (e.g., SB 209670), endothelin receptor antagonists, excitatory amino acid agonists (e.g., acylated polyarnine analogs, and N-(4-hydroxyphenylpropanonyl)-spermine analog), excitatory amino acid antagonists (e.g., Tryptophan, 4,6-disubstituted stroke & kynurenine derivatives, NPC-17742, CPC-701, and CPC-702), glutamate antagonists (e.g., Kainate quisqualate NNC-07-9202, NPC-17742, small molecule CNS-1237, NS-257, NS-072, BW-619C, CGS 19755, Riluzole, PK-26124, and RP 54274), glutamate receptor antagonists (e.g., Araxin compounds, Quinoxaline derivative, YM-90K, and YM-900), glycine antagonists, glycine NMDA agonists (e.g., 3-hydroxy-2,5-dioxo-1H-benz[b]azepines), glycine NMDA associated antagonists (e.g., 5,6-dihydro-1H-pyrrolo [1,2,3-de] quinoxaline-2,3-diones, Strychnine-insensitive glycine binding site of NMDA receptor L-687414, Glystasins, ACEA-2011, ACEA-3031, AC-1021, ACPC, and eliprodil), growth factor antagonists (e.g., non-peptide indolocarbazole neutrophic molecules, and CEP-075), GPIIb/IIIa antagonists (e.g., Peptide C68-22), hemorheological agents (e.g., Drotaverine acephyllinate, and Depogen), heparin, hydroxyl radical formation inhibitors (e.g., homopiperazine derivative K-7259), hypocalcemic agents (e.g., calcitonin peptide, related to hCGRP peptide), hypothermic agents/BMY-20862, ICAM-1 compounds (e.g., Enlimomab), immunosuppressants (e.g., small molecule compounds, and NBI-117), integrin general antagonists (e.g., monoclonal antibody AN-100225, and monoclonal antibody AN-100226), Interleukin-1 antagonists (e.g., cyclic nitrones), iron-dependent lipid peroxidation inhibitors (e.g., 2-(amino-methyl) chromans), lactic acid accumulation/inhibitors (e.g., small molecule CPC-211), Leukotriene B4 antagonists (e.g., Ebselen, DR-3305, PZ-25, PZ-51, RP 60931, and RP 61605), lipid peroxidase inhibitors (e.g., Idebenone, and Avan), low molecular weight small molecules, methyltransferase stimulants (e.g., 4-methyl benzenesulfonate, ademetionine sulfate tosilate, FO-156, and Ceritan), monoamine oxidase B inhibitors (e.g., MD-280040, MD-200243, MD-280080, Lazabemide, and Ro-19-6327), MS-153, MS-424, /Na$^+$/ H$^+$ Na$^+$/Li$^+$ exchange inhibitors (e.g., Pyrazine derivatives), nadroparin (e.g., Fraxiparin), nafronyl/ naftidrofuryl (e.g., Praxilene), nerve growth factor agonists (e.g., small molecule compounds, CNTF, BDNF, 2.5S NGF, monosialoganglioside GM1, and Sigen/ Sygen), neuronal calcium channel blockers (e.g., CPC-304, and CPC-317), neuronal differentiation compounds (e.g., F-spondin), neuropeptide agonists (e.g., Neurotrophic Peptide Trofexin), neutrophil inhibitory factors (e.g., small molecule compounds), nitric oxide agonists (e.g., hydroxy derivative N-3393, hydroxy derivative N-3398, nicorandil, and Therapicon), nitric oxide antagonists, NMDA antagonists (e.g., Spiroisoindoles/ dizocilpine derivatives, Oxindole compound, CP-112116, LY-104658, LY-235959, FR-115427, Sialic acid derivative, N-palmitoyl-Betaethylglycoside neuraminic acid, ND-37, Ro-01-6794, 706, Dextrorphan, Ifenprodil analogue eliprodil, SL-82.0715, Lipophilic molecules, HU-211, Remacemide, 934-423, 12495, 12859, 12942AA, Selfotel, CGS-19755, SDZ-EAA-494, CGP40116, CGP-37849, CGP-39551, and CGP-43487), NMDA antagonist-partial agonists (e.g., Conantokin G peptide SYM-1010), NMDA channel blockers (e.g., Aptiganel, CERESTAT, and CNS 1102), NMDA receptor antagonists, NMDA receptor subtypes (e.g., Kainate quisqua-late NNC-07-9202), non-competitive NMDA antagonists (e.g., FPL-15896), non-ionic copolymer RheothRx, nootropic/acetylcholine agonists (e.g., Oxiracetam, CT-848, and Neuractiv), norepinephrine inhibitors (e.g., Midalci-pran), N-type calcium channel antagonists (e.g., NS-626, and NS-638), opioid antagonists (e.g., Nalmefene, nalmetrene, JF-1, ORF-11676, Cervene, and Incystene), opioid kappa receptor agonists (e.g., acrylacetamide enadoline, and CI-997), organoselenims (e.g., Ebselen, DR-3305, PZ-25, PZ-51, RP 60931, and RP 61605), oxygen scavengers (e.g., Tirilazad mesylate, Lazaroids, and Freedox), PA2 inhibitors (e.g., phospholipase A2 inhibitor), PAF antagonists (e.g., nupafant, and BB-2113), partial glycine NMDA agonists (e.g., ACPC), peptide/ GPIIb/IIIa antagonists (e.g., Integrelin), peptidic neuron-specific calcium channel antagonists (e.g., SNX-111), phosphodiesterase inhibitors (e.g., Xanthine derivatives, propentofylline, Hoe-285, and Hextol), phospholipase A2 inhibitors (e.g., small organic molecule CEP-217), plasminogen activators (e.g., r-ProUK (recombinant pro-urokinase), platelet-activating factor antagonists (e.g., UK-74505), platelet adhesion inhibitors (e.g., Peptide), platelet aggregation antagonists (e.g., cilostazol, peptide agents, GPHb-IIIA inhibitor, and TP-9201), platelet aggregation inhibitors (e.g., Diaminoalkanioic acid derivatives), potassium channel agonists (e.g., Nicorandil, RP46417, SG-75, and Adancor), prolyl endopeptidase (PEP) inhibitors (e.g., JTP-4819), protein kinase C inhibitors (e.g., monosialoganglioside derivative Liga-20), proteolytic enzyme inhibitors (e.g., Protease nexin-1, Incyte, PN-1, PN-2, Nafamostat, FUT-175, Duthan, and Futhan), pyrimidine derivatives, Quinolizine derivatives (e.g., KF-17329, and KF-19863), radical formation antagonists (e.g., EPC-K1), recombinant tissue plasminogen activators (e.g., alteplase, and Activase), Schwann cell derived molecules/promoters, sigma antagonists (e.g., Sigma ligand), sigma receptor antagonists (e.g., tetrahyropyridinyl-isoxazolines and isoxazoles PD-144418), sodium/calcium channel modulators (e.g., Lifarizine, and RS-87476), sodium channel antagonists, streptokinase (e.g., Streptase), substituted guanadine (e.g., small molecule CNS-1237), superoxide dismutase stimulants (e.g., PEG conjugated enzyme superoxide dismutase/Dismutec, and PEG-SOD), thrombin inhibitors, (e.g., non-peptide), thromboxane synthase inhibitors (e.g., Linotroban, and HN-11500), thyrotropin-releasing hormone agonists (e.g., TRH agonists, Protirelin analogthymoliberin, and RX-77368,), ticlopidine (e.g., Ticlid), TJ-8007, TRH agonists (e.g., Thyrotropin releasing hormones, and JTP-2942), trilazard, urokinase (e.g., Abbokinase), w-conopeptide (e.g., SNX-111), and warfarin (e.g., Coumadin), and the like;

agents useful for the treatment of carcinomas (e.g., adriamycin, taxol, interleukin-1, interleukin-2 (especially useful for treatment of renal carcinoma), and the like, as well as leuprolide acetate, LHRH analogs (such as nafarelin acetate), and the like, which are especially useful for the treatment of prostatic carcinoma), agents useful for the treatment of endometriosis (e.g., LHRH analogs), agents useful for the treatment of uterine contraction (e.g., oxytocin), agents useful for the treatment of diuresis (e.g., vasopressin), agents useful for the treatment of cystic fibrosis (e.g., Dnase (i.e., deoxyribonuclease), SLPI, and the like), agents useful for the treatment of neutropenia (e.g., GCSF), agents useful for the treatment of lung cancer (e.g., beta 1-interferon), agents useful for the treatment of respiratory disorders (e.g., superoxide dismutase), agents useful for the treatment of ischemia/reperfusion injury (e.g., selectin inhibitors, Irf1, and the like);

agents useful for the treatment of osteoporosis (e.g., statins, such as lovastatin, pravastatin, atorvastatin, and the like; bisphosphonates; and the like);

nitric oxide synthase inhibitors (e.g., N$^4$-methyl-L-arginine, aminoguanidine, N$^G$-(iminoethyl)-L-omithine, thiocitrulline and other citrulline derivatives, N$^4$-nitro-L-arginine, N$^4$-nitro-L-arginine methyl ester, N$^4$-amino-L-arginine, and other arginine derivatives, isothiourea and its derivatives, and the like, as well as a variety of other agents, such as acyclovir, alendronate sodium, amlodipine, ampicillin, azelaic acid, azithromycin, beclomethasone, betamethasone, bicalutamide, buspirone, carisoprodol, carvedilol, cefaclor, cefadroxil, cefixime, cefprozil, ceftibuten, cefuroxime axetil, cephalexin, cetirizine hydrochloride, cimetidine, ciprofloxacin, cisapride, clarithromycin, clavulanate, clonazepam, clotrimazole, codeine, conjugated estrogens, cyclobenzaprine, desogestrel, dexrazoxane, diazepam, dicyclomine HCl, digoxin, diltiazem, dirithromycin, doxazosin, doxycycline, enalapril, erythromycin, erythromycin base, erythromycin stearate, estradiol, ethinyl estradiol, ethynodiol diacetate, etodolac, famotidine, fluconazole, fluoxetine, fluvastatin, furosemide, gemfibrozil, glipizide, glyburide, guaifenesin, hydrochlorothiazide, hydrocodone, hydrocortisone, ibuprofen, ibutilide fumarate, indapamide, insulin, ipratropium bromide, ketoconazole, ketoprofen, ketorolac tromethamine, lamivudine, lansoprazole, levonorgestrel, levothyroxine, lisinopril, loracarbef, loratidine, lorazepam, losartan potassium, lovastatin, medroxyprogestrone, methylphenidate, methylprednisolone, metoprolol, metoprolol tartrate, moexipril hydrochloride, mometasone furoate, mupirocin, mycophenolate mofetil, nabumetone, nalmefene hydrochloride, naproxen, neomycin, nifedipine, nisoldipine, nitrofurantoin, nizatidine, norethindrone, norgestrel, nortriptyline, ofloxacin, omeprazole, oxaprozin, oxycodone, paroxetine, penicillin, pentoxifylline, phenylpropanolamine, phenytoin, polymyxin, porfimer sodium, potassium chloride, pravastatin, prednisone, promethazine, propoxyphene, pseudoephedrine, quinapril, ramipril, ranitidine, riluzole, salmeterol, saquinavir mesylate, sertraline, sevoflurane, simvastatin, sucralfate, sulfamethoxasole, sumatriptan, temazepam, terazosin, terconazole, terfenadine, tetracycline, theophylline, timolol, trarnadol, tramadol hydrochloride, tretinoin, triamcinolone acetonide, triamterene, trimethoprim, valproic acid, venlafaxine, verapamil, wafarin, zolpidem, and the like.

The nitric oxide scavenging component (e.g., dithiocarbamate component) and the pharmacalogically active agent of invention conjugates can be directly or indirectly covalently attached employing a variety of linkages (optionally including a linker), e.g., ester linkages, disulfide linkages, amide linkages, ether linkages, thioether linkages, imide linkages, sulfate ester linkages, sulfonate ester linkages, phosphate ester linkages, carbonate linkages, O-glycosidic linkages, S-glycosidic linkages, and the like. Such linkages can be accomplished using standard synthetic techniques as are well known by those of skill in the art, either by direct reaction of the starting materials, or by incorporating a suitable functional group on the starting material, followed by coupling of the reactants.

In accordance with another embodiment of the present invention, there are provided methods for the preparation of protected forms of pharmacologically active agents, said method comprising covalently attaching a suitable nitric oxide scavenger (e.g., dithiocarbamate) to said pharmacologically active agent. The resulting conjugate provides a latent form of the pharmacologically active agent, releasing the biological activity thereof only when the nitric oxide scavenger component of said conjugate (optionally including the linker referred to above) is cleaved from said pharmacologically active agent (e.g., by an esterase, amidase or other suitable enzyme). Cleavage of the dithiocarbamate from said pharmacologically active agent may also release free dithiocarbamate, which would provide effective nitric oxide scavenging activity directly at the site where nitric oxide production is commonly induced as a result of the disease state being treated and/or as a result of the treatment itself.

As readily recognized by those of skill in the art, invention conjugates can be prepared in a variety of ways. See, for example, Scheme 1, wherein a pharmacologically active compound (1) bearing a carboxylic moiety can be reacted with a diol (2) under conditions suitable to produce ester (3), which can then be activated by treatment with an arylsulfonyl chloride under conditions suitable to produce compound (5), which can then be coupled with the salt form of a dithiocarbamate (e.g., compound 6B or disulfide thereof such as compound 6A) to produce invention conjugate (7).

SCHEME 1

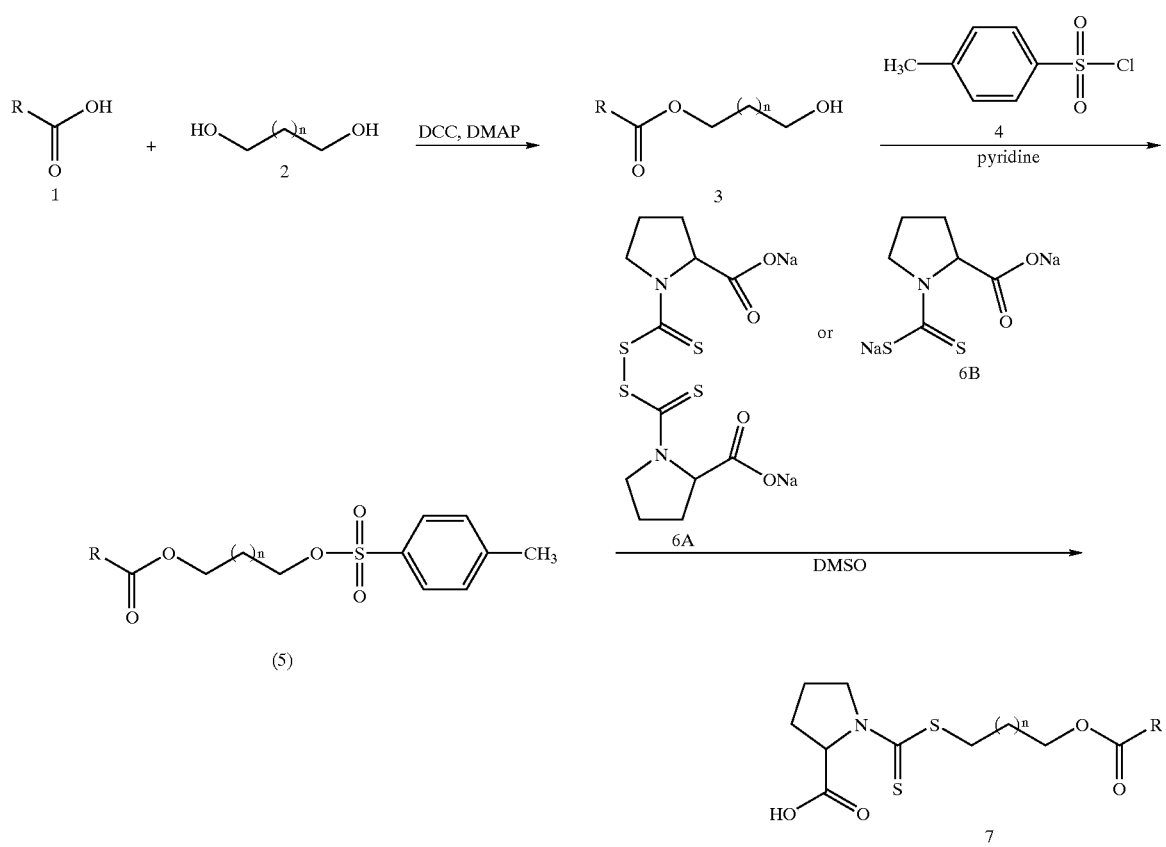

Employing this general reaction scheme, invention conjugates can be prepared from a wide variety of pharmacologically active agents. See, for example, Examples 6, 7, 8 and 9 provided herein.

In accordance with yet another embodiment of the present invention, there are provided methods for reducing the side effects induced by administration of pharmacologically active agent(s) to a subject, said method comprising covalently attaching a suitable nitric oxide scavenger (e.g., dithiocarbamate) to said pharmacologically active agent(s) prior to administration to said subject.

In accordance with still another embodiment of the present invention, there are provided methods for enhancing the effectiveness of pharmacologically active agent(s), said method comprising covalently attaching a suitable nitric oxide scavenger (e.g., a dithiocarbamate) to said pharmacologically active agent.

In accordance with a still further embodiment of the present invention, there are provided improved methods for the administration of pharmacologically active agent(s) to a subject for the treatment of a pathological condition, the improvement comprising covalently attaching a dithiocarbamate to said pharmacologically active agent prior to administration of said pharmacologically active agent to said subject.

Those of skill in the art recognize that the nitric oxide scavenger-containing conjugates described herein can be delivered in a variety of ways, such as, for example, orally, intravenously, subcutaneously, parenterally, rectally, by inhalation, and the like.

Depending on the mode of delivery employed, the conjugates contemplated for use herein can be delivered in a variety of pharmaceutically acceptable forms. For example, the conjugate can be delivered in the form of a solid, solution, emulsion, dispersion, micelle, liposome, and the like.

Thus, in accordance with still another embodiment of the present invention, there are provided physiologically active composition(s) comprising invention conjugates in a suitable vehicle rendering said conjugates amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound(s) (e.g., one or more pharmacologically active agents, covalently bound to a dithiocarbamate of structure I) is(are) included in the pharmaceutical composition in an amount sufficient to produce the desired effect upon the process or disease condition.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Conjugates contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In general, the dosage of nitric oxide scavenger-containing conjugate of the invention employed as described herein falls in the range of about 0.01 mmoles/kg body weight of the subject/hour up to about 0.5 mmoles/kg/hr. Typical daily doses, in general, lie within the range of from about 10 g up to about 100 mg per kg body weight, and, preferably within the range of from 50 g to 10 mg per kg body weight and can be administered up to four times daily. The daily IV dose lies within the range of from about 1 g to about 100 mg per kg body weight, and, preferably, within the range of from 10 g to 10 mg per kg body weight.

In accordance with yet another embodiment of the present invention, there are provided improved methods for the treatment of a subject suffering from a pathological condition by administration thereto of pharmacologically active agent(s), the improvement comprising covalently attaching a dithiocarbamate to said pharmacologically active agent prior to administration thereof to said subject.

Thus, invention method for the treatment of a subject afflicted with a pathological condition comprises administering to a subject an effective amount of a modified pharmacologically active agent, wherein said pharmacologically active agent is effective for treatment of said condition, and wherein said pharmacologically active agent has been modified by the covalent attachment thereto of a dithiocarbamate.

The invention will now be described in greater detail by reference to the following non-limiting examples.

EXAMPLE 1

Preparation of the Ester Conjugate of Pyrrolidinol and Ibuprofen

To 200 ml of methylene chloride in a 500-ml reaction vessel was added 24 grams of ibuprofen (α-methyl-4-(2-methylpropyl)benzene-acetic acid), 10 grams of 2-pyrrolidinol and 0.5 grams of a suitable coupling agent, e.g., dicyclohexylcarbodiimide. The reaction proceeds at room temperature for 1 to 3 hours with stirring. The ester conjugate is isolated and purified with a 60–70% yield.

EXAMPLE 2

Conversion of the Ester Conjugate of Pyrrolidinol and Ibuprofen to the Ester Conjugate of Pyrrolidinol Dithiocarbamate and Ibuprofen To 100 ml of methanol in a 500-ml reaction vessel was added 10 grams of the ester conjugate obtained from Example 1. An aqueous NaOH solution (6.9 grams in 10 ml water) is added dropwise to the reaction mixture at 4° C. The reaction is allowed to proceed for one additional hour at 4° C. A solution mixture of carbon disulfide (5 ml) and ethanol (15 ml) is added dropwise to the above reaction mixture with slow stirring at 4° C. The fmal product is isolated and purified with a yield of about 70%.

EXAMPLE 3

Preparation of the Ester Conjugate of L-proline and Adriamycin

To 200 ml of methylene chloride in a 500-ml reaction vessel was added 47.2 grams of adriamycin, 10 grams of L-proline and 0.5 grams of any suitable coupling agent, e.g., dicyclohexylcarbodiimide. The reaction is allowed to proceed at room temperature for 1 to 3 hours with stirring. The ester conjugate is isolated and purified with about 70% yield.

EXAMPLE 4

Conversion of the Ester Conjugate of L-proline and Adriamycin to the Ester Conjugate of L-proline Dithiocarbamate and Adriamycin To 100 ml of methanol in a 500-ml reaction vessel was added 10 grams of the ester conjugate obtained from Example 3. An aqueous NaOH solution (6.9 grams in 10 ml) water is added dropwise to the reaction mixture at 4° C. The reaction is allowed to proceed for one additional hour at 4° C. A solution mixture of carbon disulfide (5 ml) and ethanol (15 ml) is added dropwise to the above reaction mixture with slow stirring at 4° C. The final product is isolated and purified with a yield of about 70%.

EXAMPLE 5

General Procedure for the Preparation of Invention Conjugates

5A. General procedure for the preparation of intermediate 3 (Scheme 1). To a stirring solution of pharmacologically active compound (1) (1 eq), diol compound (2) (5 eq) and dimethylaminopyridine (DMAP) (0.2 eq) in anhydrous THF is added 1,3-dicyclohexylcarbodiimide (DCC) (1 eq) at 0° C. The resulting solution is stirred at room temperature for several hours. The reaction solution is filtered and the solvent is evaporated. The residue is partially dissolved in ethyl acetate and the solid is filtered off and the solution is washed with 0.5 N HCl, saturated sodium bicarbonate solution and brine. After the solvent is evaporated, the compound is purified either by flash chromatography or recrystallization to give compound 3.

5B. General procedure for the preparation of intermediate 4 (Scheme 1). To a solution of compound 3 (1 eq) in pyridine is added p-toluenesulfonyl chloride (4) (2 eq) at 0° C. The resulting solution is put in the refrigerator (~4° C.) for three days. The reaction solution is poured onto ice and extracted with ether. The combined ether solution is washed with water and dried. After the solvent is evaporated, the residue is purified by appropriate means to give compound 5.

5C. General procedure for the preparation of conjugate compound 7. (Scheme 1). A solution of intermediate 5 and compound 6A or 6B in DMSO is stirred at room temperature under argon for one to three hours. The reaction solution is poured onto ice and extracted with ether. The combined ether solution is washed with water. The ether is dried and evaporated and the residue is purified by appropriate means to give the conjugate compound 7.

EXAMPLE 6

Synthesis of Invention Conjugate of Naproxen 6A. 3-Hydroxypropyl (S)-(+)-methoxy-α-methyl-2-naphthaleneacetate 10 (Scheme 2). To a stirring solution of (S)-(+)-methoxy-α-methyl-2-naphthaleneacetic acid (naproxen, 8) (10.4 g, 45 mmol), propanediol (9) (17.1 g, 225 mmol) and DMAP (0.54 g, 4.5 mmol) in anhydrous THF (300 mL) is added DCC (9.4 g, 45 mmol) at 0° C. The resulting solution is stirred at 0° C. for 10 min and then at room temperature for 5 h. The reaction solution is filtered and the solvent is evaporated. The residue is partially dissolved in ethyl acetate and the solid is filtered off and the solution is washed with 0.5 N HCl, saturated sodium bicarbonate solution and brine. The organic phase is dried ($Na_2SO_4$) and the solvent is evaporated. The residue is purified by recrystallization from 1:3 hexanes-dichloromethane to give 9.7 g (75%) of compound 10 as a white solid; $^1H$ NMR ($CDCl_3$) 1.58 (d, 3H), 1.78 (m, 2H), 1.88 (t, 1H, ex $D_2O$), 3.53 (m, 2H), 3.87 (q, 1H), 3.90 (s, 3H), 4.2 (m, 2H), 7.11–7.15 (m, 2H), 7.39 (d, 1H), 7.65 (s, 1H), 7.70 (d, 2H); MS (ES) m/z 289.2 (M+H )$^+$ (C$_{17}$H$_{22}$O$_4$ requires 289.34).

6B. 3-Tosylpropyl (S)-(+)-methoxy- -methyl-2-naphthaleneacetate 11 (Scheme 2). To a stirring solution of compound 10 (8.6 g, 30 mmol) in 35 mL of pyridine is added tosyl chloride (4) (11.43 g, 60 mmol) at 0° C. The resulting solution is put in the refrigerator (~4° C.) for three days. The reaction solution is poured onto 300 g ice and extracted with ether. The combined ether solution is washed with 10% HCl solution, saturated NaHCO$_3$ solution and brine. The solution is dried (Na$_2$SO$_4$) and evaporated. The residue is purified by flash chromatography on a silica gel column using 100% CH$_2$Cl$_2$ as the eluent to give 8.92 g (67%) of compound 11 as a pale yellow oil; $^1$H NMR (CDCl$_3$) 1.53 (d, 3H), 1.90 (m, 2H), 2.42 (s, 3H), 3.78 (q, 1H), 3.91 (s, 3H), 3.99 (m, 1H), 4.09 (t, 2H), 7.11–7.15 (m, 2H), 7.25–7.28 (m, 2H), 7.32–7.34 (m, 1H), 7.64 (m, 1H), 7.65–7.71 (m, 4H); MS (ES) m/z 443.3 (M+H)$^+$ (C$_{24}$H$_{27}$O$_6$S requires 443.53).

6D. Compound 12 from Compound 6B (Scheme 2). To a stirring solution of compound 5 (2.21 g, 5mmol) in 10 mL of anhydrous DMSO is added compound 6B (1.06, 4.5 mmol) at room temperature. The resulting solution is stirred at room temperature for 80 min. The reaction solution is poured into water and washed with ether. The aqueous solution is acidified to pH=3–4 using concentrated HCl solution and extracted with dichloromethane. The combined organic phase is washed with water and brine. The organic phase is dried over Na$_2$SO$_4$ and the solvent is evaporated under high vacuum to give 1.3 g (63%) of the compound 12. Compound 12 from this procedure has the same $^1$H NMR and MS spectra with the compound from the above procedure using compound 6A.

The synthetic steps described in this example are illustrated in Scheme 2:

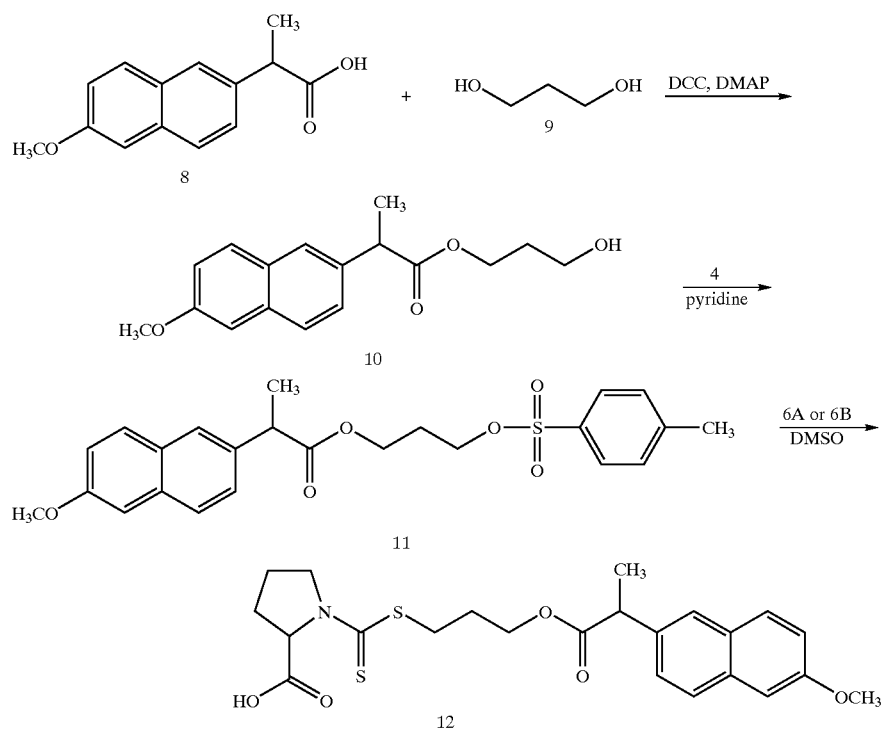

SCHEME 2

6C. Compound 12 from Compound 6A (Scheme 2). To a stirring solution of compound 11 (8.86 g, 20.02 mmol) in 35 mL of DMSO is added compound 6A (3.86 g, 9.1 mmol) at room temperature. The resulting solution is stirred at room temperature for 70 min. The reaction solution is poured onto 100 g ice and extracted with ether. The combined ether solution is washed with water and brine. The solution is dried (Na$_2$SO$_4$) and evaporated. The residue is purified by flash chromatography on a silica gel column using 200:1 and then 20:1 CH$_2$Cl$_2$—CH$_3$OH as eluents to give 3.74 g (45%) of compound 12 as a white foam; $^1$H NMR (CDCl$_3$) 1.57(d, 6H), 1.94–2.20 (m, 12H), 3.20–3.25 (m, 4H), 3.57–3.59 (m, 2H), 3.72–3.79 (m, 2H), 3.84–3.88 (m, 2H), 3.90 (s, 6H), 5.05 (m, 2H), 7.10–7.14 (m, 4H), 7.39–7.41 (d, 2H), 7.65–7.70 (m, 6H); MS (ES) m/z 921.5 M$^+$ (C$_{46}$H$_{52}$N$_2$O$_{10}$S$_4$ requires 921.2)

EXAMPLE 7

Synthesis of Invention Conjugate of Ibuprofen 7A. 3-Hydroxypropyl (S)-(+)-4-isobutyl-α-methylphenylacetate 14 (Scheme 3). Compound 14 is prepared as described above for compound 10 from (S)-(+)-4-isobutyl-α-methylphenylacetic acid (ibuprofen, 13) (4.12 g, 20 mmol) and propanediol (7.6 g, 100 mmol). The compound is purified by flash chromatography on a silica gel column using 10:1 and then 3:1 hexanes-ethyl acetate as eluents to give 3.54 g (65%) of compound 14 as a colorless oil; $^1$H NMR (CDCl$_3$) 0.89 (d, 6H), 1.49 (d, 3H), 1.80 (m, 2H), 1.76–1.85 (m, 2H, 1H ex D$_2$O), 2.45 (m, 2H), 3.52 (m, 2H), 3.70 (q, 1H), 4.21 (m, 2H), 7.10 (d, 2H), 7.18 (d, 2H); MS (ES) m/z 265.7(M+H)$^+$ (C$_{16}$H$_{25}$O$_3$ requires 265.36).

7B. 3-Tosylpropyl (S)-(+)4-isobutyl-α-methylphenylacetate 15 (Scheme 3). Compound 15 is prepared as described above for compound 11 from compound 14 (1.76 g, 0.56 mmol) and tosyl chloride (4) (0.5 g, 1.13 mmol). The compound is purified by flash chromatography on a silica gel column using CH$_2$Cl$_2$ as the eluent to give 1.5 g (54%) of the compound 15 as a colorless oil; $^1$H NMR (CDCl$_3$) δ0.88 (d, 6H), 1.43 (d, 3H), 1.80–1.92 (m, 3H), 2.44 (d, 2H), 2.45 (s, 3H), 3.61 (q, 1H), 3.99 (t, 2H), 4.08 (t, 2H), 7.07 (d, 2H), 7.13 (d, 2H), 7.33 (d, 2H), 7.75 (d, 2H); MS (ES) m/z 441.3 (M+Na)$^+$ (C$_{23}$H$_{30}$O$_5$SNa requires 441.55).

7C. Compound 16 (Scheme 3). Compound 16 is prepared as described above for compound 12 from compound 15 (1.35 g, 3.2 mmol) and compound 6A (0.7 g, 1.6 mmol) or 6B (0.75 g, 3.3 mmol) in DMSO. The compound is purified by flash chromatography on a silica gel column using 200:1 and then 20:1 CH$_2$Cl$_2$—CH$_3$OH as eluents to give 0.55 g (40%) of compound 16 as a pale yellow oil; $^1$H NMR (CDCl$_3$) δ0.89 (d, 6H), 1.49 (d, 3H), 1.84 (m, 1H), 2.00 (m, 2H), 2.17–2.32 (m, 4H), 2.44 (d, 2H), 3.23 (m, 2H), 3.71 (m, 2H), 3.81 (m, 1H), 7.08 (d, 2H), 7.24 (d, 2H); MS (ES) m/z 873.2 M$^+$ (C$_{44}$H$_{60}$N$_2$O$_8$S$_4$ requires 873.22).

The synthetic steps discribed in this example are illustrated in Scheme 3:

SCHEME 3

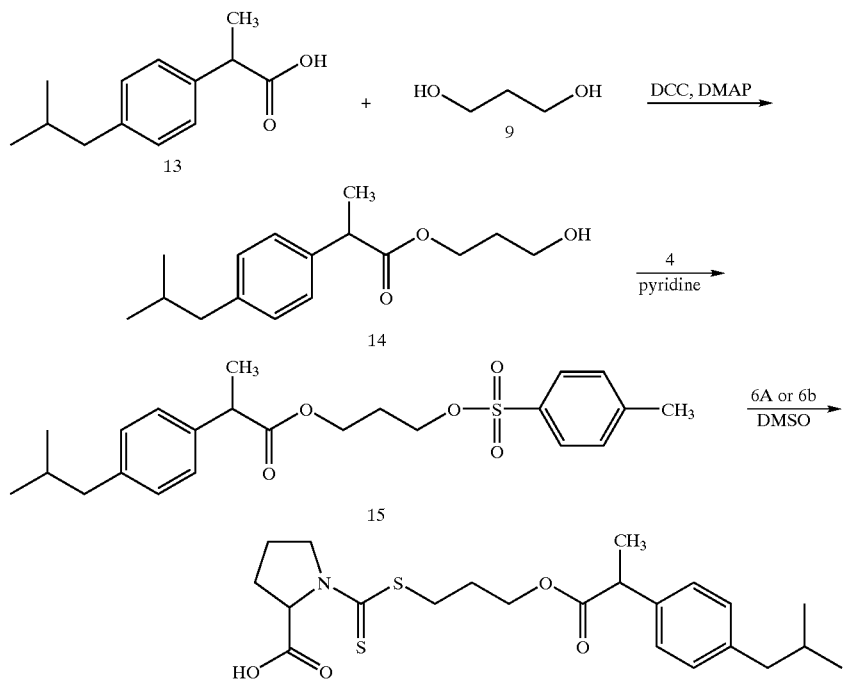

EXAMPLE 8
Synthesis of Invention Conjugate of Ketoprofen 8A. 3-Hyroxypropyl (S)-(+)-3-benzoyl-α-methylbenzeneacetate 18 (Scheme 4). Compound 18 is synthesized as described above for compound 10 from (S)-(+)-3-benzoyl-α-methylbenzeneacetic acid (ketoprofen, 17) (3.8 g, 15 mmol) and propanediol (9) (5.7 g, 75 mmol). The compound is purified by flash chromatography on a silica gel column using 200:1 CH$_2$Cl$_2$—MeOH as the eluent to give 2.63 g (56%) of the compound 18 as a colorless oil; $^1$H NMR (CDCl$_3$) δ1.54 (d, 3H), 1.82 (m, 2H), 1.82–1.82 (b, 1H, ex D$_2$O), 3.58 (m, 2H), 3.79–3.83 (q, 1H), 4.25 (m, 2H), 7.42–7.80 (m, 9H); MS (ES) m/z 313.1 (M+H)$^+$ (C$_{19}$H$_{21}$O$_4$ requires 313.3).

8B. 3-Tosylpropyl (S)-(+)-3-benzoyl-α-methylbenzeneacetate 19 (Scheme 4). Compound 19 is synthesized as described above for compound 11 from compound 18 (2.48 g, 7.94 mmol) and compound 4 (3.03 g, 15.9 mmol). The compound is purified by flash chromatography on a silica gel column using 6:1 and then 4:1 hexanes-ethyl acetate as eluents to give 2.72 g (74%) of the compound 19 as a colorless oil; $^1$H NMR (CDCl$_3$) δ1.49 (d, 3H), 1.94 (m, 2H), 2.43 (s, 3H), 3.73 (q, 1H), 4.01 (t, 2H), 4.11 (t, 2H), 7.31–7.79 (m, 13H); MS (ES) m/z 467.3 (M+H)$^+$ ($C_{26}H_{27}O_6S$ requires 467.55).

8C. Compound 20 (Scheme 4). Compound 20 is prepared as described above for compound 12 from compound 6A (0.91 g, 2.15 mmol) or 6B (1.01 g, 4.3 mmol) and compound 19 (2.0 g, 4.30 mmol) in 9 ml of DMSO. The compound is purified by flash chromatography on a silica gel column using 3:1 hexanes-ethyl acetate and then 20:1 $CH_2Cl_2$—MeOH as eluents to give 1.21 g (58%) of the compound as a pale yellow oil; $^1$H NMR (CDCl$_3$) δ1.44 (d, 3H), 1.82–2.11 (m, 6H), 3.12–3.28 (m, 2H), 3.59–3.72 (m, 2H), 3.61–3.75 (m, 2H), 3.90–4.15 (m, 3H), 4.85 (m, 1H), 7.51–7.73 (m, 9H); MS (ES) m/z 969.5 (M+H)$^+$ ($C_{50}H_{53}N_2O_{10}S_4$ requires 969.22).

The synthetic steps described in this example are illustrated in Scheme 4:

6.86 (d, 1H), 6.95 (d, 1H), 7.48 (d, 2H), 7.66 (d, 2H); MS (ES) m/z 416.5 (M+H)$^+$ ($C_{22}H_{23}ClNO_5$ requires 416.87).

9B. 3-Tosylpropyl 1-(p-chlorobenzoyl)-5-methoxy-2-methylindole-3-acetate 23 (Scheme 5). Compound 23 is prepared as described above for compound 11 from compound 22 (0.96 g, 2.3 mmol) and compound 9 (0.88 g, 4.6 mmol). The compound is purified by flash chromatography on a silica gel column using 3:1 hexanes-ethyl acetate as the eluent to give 0.93 g (71%) of the compound 23 as a pale yellow oil; $^1$H NMR (CDCl$_3$) δ1.98 (m, 2H), 3.62 (s, 2H), 3.82 (s, 3H), 4.05 (t, 2H), 4.14 (t, 2H), 6.67 (d, 1H), 6.90 (d, 1H), 6.93 (d, 1H), 7.32 (d, 2H), 7.47 (d, 2H), 7.66 (d, 2H), 7.74 (d, 2H); MS (ES) m/z 592.0 (M+Na)$^+$ ($C_{29}H_{28}ClNO_7$SNa requires 592.13).

9C. Compound 24 (Scheme 5). Compound 24 was prepared as described above for compound 12 from compound 23 (0.89 g, 1.56 mmol) and compound 6A (0.33 g, 0.78

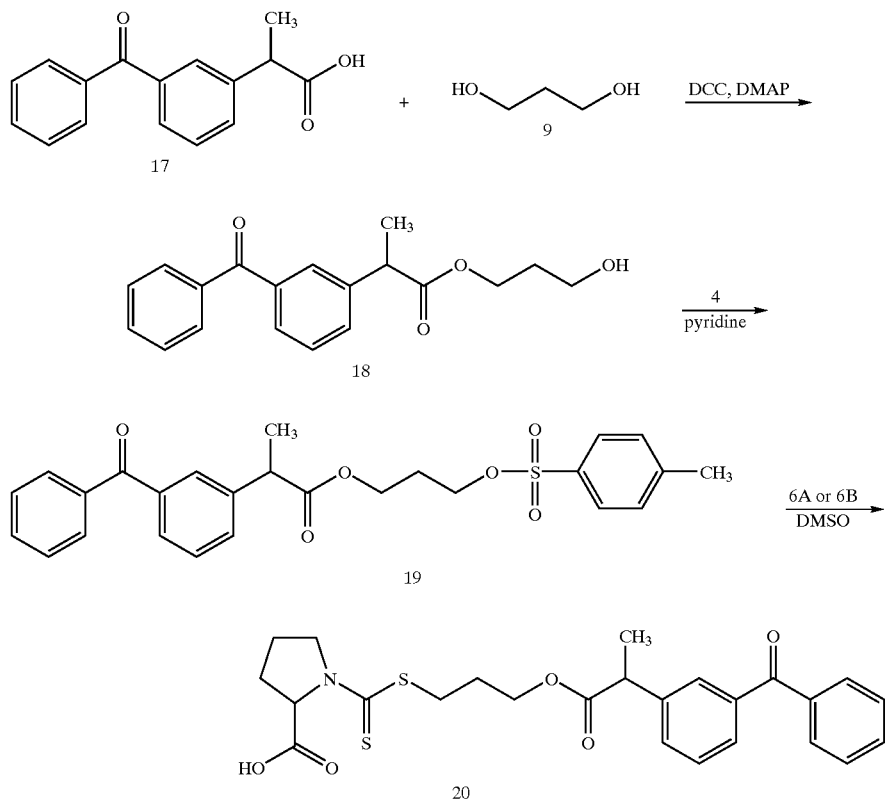

SCHEME 4

EXAMPLE 9
Synthesis of Invention Conjugate of Indomethacin 9A. 3-Hydroxypropyl 1-(p-chlorobenzoyl)-5-methoxy-2-methylindole-3-acetate 22 (Scheme 5). Compound 22 is prepared as described above for compound 10 from 1-(p-chlorobenzoyl)-5-methoxy-2-methylindole-3-acetic acid (indomethacin, 21) (1.8 g, 5.0 mmol) and propanediol (9) (1.9 g, 25 mmol). The compound is purified by flash chromatography on a silica gel column using 200:1, 100:1 and 50:1 $CH_2Cl_2$—MeOH as eluents to give 1.02 g (49%) of the compound 22 as a pale yellow oil; $^1$H NMR (CDCl$_3$) δ1.70 (t, 1H, ex D$_2$O), 1.86 (m, 2H), 2.39 (s, 3H), 3.63 (q, 2H), 3.68 (s, 2H), 3.84 (s, 3H), 4.27 (t, 2H), 6.67 (d, 1H), mmol) or 6B (0.37 g, 1.56 mmol). The compound is purified by flash chromatography on a silica gel column using 200:1 and then 20:1 $CH_2Cl_2$—MeOH as eluents to give 0.33 g (36%) of the compound 24 as a white foam; $^1$H NMR (CDCl$_3$) δ2.01–2.30 (m, 6H), 2.38 (s, 3H), 3.29 (t, 2H), 3.68 (m, 4H), 3.84 (s, 3H), 4.19 (t, 2H), 5.13 (t, 1H), 6.66 (m, 1H), 6.87 (d, 1H), 6.96 (d, 1H), 7.46 (d, 2H), 7.66 (d, 2H); MS (ES) m/z 1177.5 (M+H)$^+$ ($C_{54}H_{53}Cl_2N_4O_{12}S_4$ requires 1177.2).

The systhetic steps described in this example are illustrated in Scheme 5:

SCHEME 5

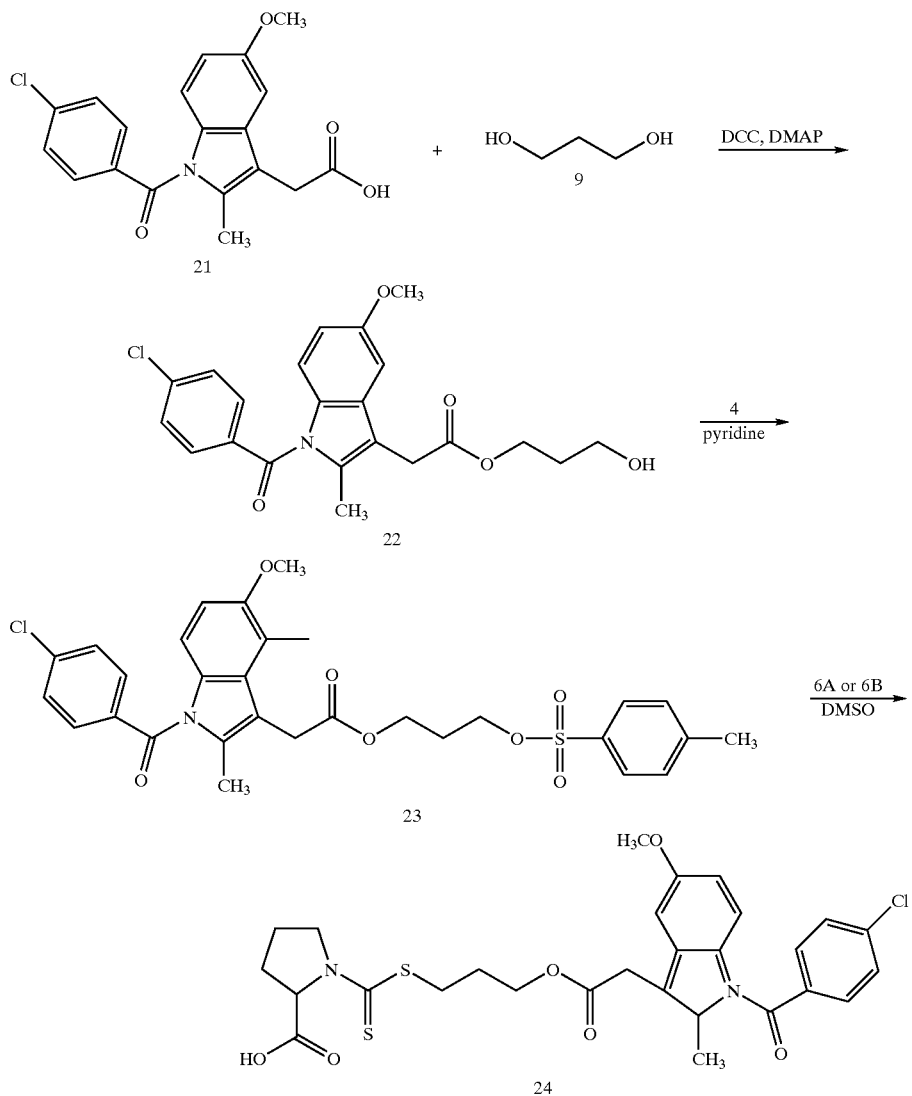

EXAMPLE 10
Enzymatic Hydrolysis of Invention Conjugates

10A. Enzymatic hydrolysis of compound 12. Compound 12 (4.6 mg, 0.0049 mmol) was dissolved in 0.25 ml of DMSO to make a 0.02M solution. The above solution (0.05 mL) was transferred to 1 mL of PBS buffer and mixed with 33.3 units of the esterase. The resulting solution was put in a water bath (37° C.) for 30 min and then at rt overnight. The compound was decomposed into two compounds; Silica gel TLC $R_f$ 0.46 (naproxen) and $R_f$ 0.12 (20:1 $CH_2Cl_2$—MeOH).

10B. Enzymatic hydrolysis of compound 16. Compound 16 was hydrolyzed as described above for compound 12. The compound 16 was decomposed into two compounds within 5 h; Silica gel TLC $R_f$ 0.64 (ibuprofen) and $R_f$ 0.12 (20:1 $CH_2Cl_2$—MeOH).

10C. Enzymatic hydrolysis of compound 20. Compound 20 was hydrolyzed as described above for compound 12. The compound 20 was decomposed into two compounds within 5 h; Silica gel TLC $R_f$ 0.45 (ketoprofen) and $R_f$ 0.12 (20:1 $CH_2Cl_2$—MeOH).

10D. Enzymatic hydrolysis of compound 24. Compound 24 was hydrolyzed as described above for compound 12. The compound 24 was decomposed into two compounds within 5 h; Silica gel TLC $R_f$ 0.44 (indomethacin) and $R_f$ 0.12 (20:1 $CH_2Cl_2$—MeOH).

EXAMPLE 11
Evaluation of the Effects of the Conjugate of Pyrrolidinol Dithiocarbamate and Ibuprofen (PDI) on the Acute Gastric Mucosal Injury Wistar rats (200–250 grams, male) are fasted overnight but allowed free access to water. Ten rats in each group are given ibuprofen or PDI orally at doses of 10, 20 or 50 mg/kg. The rats are sacrificed five hours later and visible gastric damage is assessed by examining under microscope and histological evaluation.

EXAMPLE 12
Evaluation of the Effects of the Conjugate of Pyrrolidinol Dithiocarbamate and Ibuprofen (PDI) on Chronic Gastric Ulcer White New Zealand rabbits (male, about 1 kg) are given subcutaneously ibuprofen or PDI at a dose of 30 mg/kg for every 12 hours. The animals are sacrificed on day 4 (after the 7th dose) and the visible ulcers in the stomach are examined and measured with calipers. The tissue samples are fixed in neutral buffered formalin and processed for histological evaluation.

EXAMPLE 13

Evaluation on the Anti-inflammatory Effects of the Conjugate of Pyrrolidinol Dithiocarbamate and Ibuprofen (PDI)

Wistar rats (male, 200–250 g) are fasted overnight but allowed to free access to drinking water. Ibuprofen or PDI is given orally at a dose of 1, 10, or 30 mg/kg (6 animals each group). After one hour, the rats are anesthetized and 0.1 ml of lambda carrageenan (0.1% solution) is injected into the right hind foot pad. The volume of the pad is measured by hydroplethysmometry every hour for the next five hours.

EXAMPLE 14

Evaluation of the Effects of the Conjugate of Pyrrolidinol Dithiocarbamate and Ibuprofen (PDI) on Prostaglandin Synthesis Wistar rats (male, 200–250 g) are fasted overnight but allowed free access to drinking water. The rats are anesthetized and their backs are shaved. After an incision to the back, a sponge (2.5×1×0.5 cm) soaked with 2 ml of 0.5% carrageenan is implanted. Five hours later, the rats (6 animals in each group) are given orally either ibuprofen or PDI at a dose of 30 mg/kg or vehicle control. One hour later, the rat is sacrificed and the sponge is carefully removed. The exudate is recovered from the sponge and the prostaglandin E2 level in the exudate is measured by enzyme-linked immunosorbent assay.

EXAMPLE 15

Evaluation on the Protective Effects of the Conjugate of L-proline Dithiocarbamate and Adriamycin (PDA) Against Adriamycin-induced Cardiotoxicity Balb/c mice (male, 20–25 g) are fed a standard diet and allowed free access to drinking water. The mice are anesthetized and the telemetry system consisting of implantable transmitters, a telemetry receiver and analog ECG adapter is implanted in the peritoneal cavity of each mouse. After surgery, the mice are allowed to recover for two weeks. The mice are given intravenously either adriamycin or PDA at a dose of 4 mg/kg through the tail vein. The treated mice are observed for two weeks. The body weight, ECG and heart rate are recorded daily. At the end of the study, the animals are sacrificed and the hearts are processed for histological evaluation.

EXAMPLE 16

Reduced Numbers of Gastric Erosions in the Rat Gastropathy Model By Naproxen-derived Conjugate of the Invention The main side effect of NSAIDs is gastrointestinal ulceration and intolerance. Gastric damage from orally dosed NSAIDs has both local erosive and systemic ulcerative components. The ability to cause local erosions can be estimated by using the rat gastropathy model (Brand, S J et al. supra). Sprague-Dawley rats (male, 175–250 g), were food fasted overnight and then dosed orally with 5 to 10 ml/kg of drug, followed by removal of drinking water. After 2.5 hours, the rats were injected i.v. with Evans Blue to stain the gastric erosions. Thirty minutes later the animals were sacrificed by $CO_2$ inhalation and the stomachs removed, opened along the greater curvature, and washed with water. The total number of blue lesions was counted and the length of the lesions noted.

Administration of Naproxen at 15 and 30 mg/kg and equimolar doses of Naproxen—containing conjugate of the invention (27 & 54 mg/kg) resulted in a dose-related number of lesions for both compounds (FIG. 1). Most of the lesions were linear or oval in shape and less than 2 mm in length; they were found primarily in the corpus of the stomach. The group subjected to high dose of the Naproxen—containing conjugate of the invention had significantly fewer lesions than the high dose naproxen group (ANOVA; p<0.005). The group subjected to low dose Naproxen—containing conjugate of the invention also showed fewer erosions than the low dose of naproxen, but statistical significance was not achieved with only 6 animals in each group. These results suggest that the naproxen prodrug, i.e., Naproxen—containing conjugate of the invention, has the ability to reduce the number of erosions in the corpus of the stomach after oral administration in the rat.

EXAMPLE 17

Reduction of Acute Hindlimb Inflammation in the Rat Carrageenan-induced Hindlimb Edema Model by Naproxen Containing Conjugates of the Invention Efficacy of NSAIDs in acute inflammation can be estimated by using intraplantar injection of carrageenan in the rat. Male Sprague-Dawley rats (200–250 g) were injected intradermally in the footpad with 50 μl of a 1% carrageenan solution in PBS. Swelling of the injected paw was measured at 2, 3, 5 & 7 hours using a plethysmometer.

Figure 2:
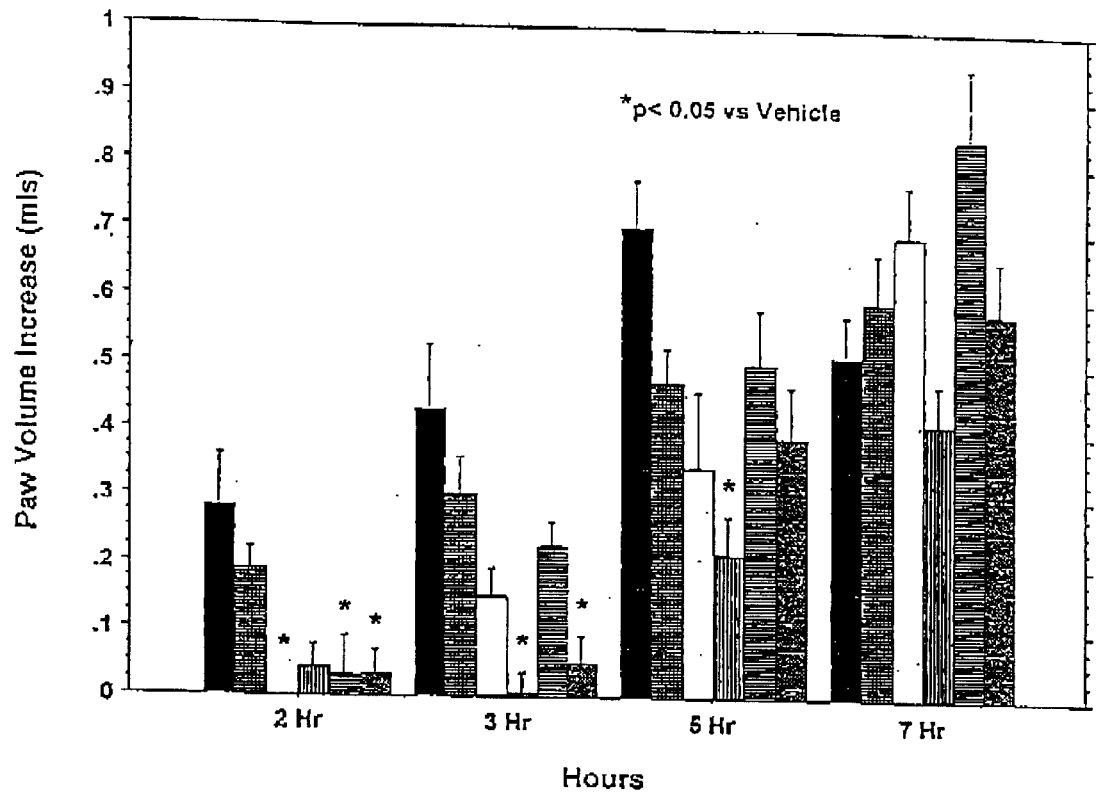
FIG. 2 illustrates the alleviation of acute inflammation by Naproxen prodrug according to the invention in a carrageenen model in rats. Paw volume increases (measured with a Plethysmometer) are reported as a function of time, and were measured on the injected feet of male Sprague-Dawley rats which had been pretreated at −1 hour with oral vehicle, naproxen or Naproxen prodrug, then injected transdermally with 1% carrageenen. Blackened boxes represent untreated animals, checkered boxes represent animals to whom vehicle (5% DMSO/CMC) was administered, open boxes represent naproxen administration at 3 mg/kg, vertically lined boxes represent naproxen administration at 10 mg/kg, horizontally lined boxes represent Naproxen prodrug administration at 5.5 mg/kg (molar equivalent of 3 mg/kg naproxen alone), and diagonally cross-hatched boxes represent Naproxen prodrug/kg (molar equivalent of 10 mg/kg naproxen alone).

Pretreatment with oral naproxen given one hour before the carrageenan injection at 10 mg/kg resulted in a significant reduction in swelling that lasted from 2 to 5 hours post injection (FIG. 2). An equimolar dose of Naproxen—containing conjugate of the invention (18 mg/kg) reduced inflammation significantly at 2 and 3 hours, but started to wear off by 5 hours. These results suggest that Naproxen—containing conjugate of the invention is orally active in rats, but slightly less effective vs acute inflammation than the parent drug.

Conclusions: Oral Naproxen—containing conjugates according to the invention have antiinflammatory activity similar to naproxen in the chronic adjuvant arthritis and acute carrageenan hindlimb edema rat models. The tendency to cause gastric erosions is reduced in Naproxen—containing conjugates according to the invention. Thus, Naproxen—containing conjugates according to the invention may be effective prodrug form of naproxen with reduced gastric side effects.

EXAMPLE 18

Reduction of Chronic Hindlimb Inflammation in the rat Adjuvant Arthritis Model by Naproxen—Containing Conjugates of the Invention NSAIDs are useful in both chronic and acute inflammatory conditions. Efficacy in chronic inflammation can be estimated using the rat adjuvant arthritis model (Blackham et al. supra). In this model Lewis male rats (175–250 g) were injected intradermally in the footpad with M. tuberculosis powder suspended in mineral oil at 5 mg/ml. Progressive swelling of the uninjected paw and ankle joint between days 11 and 15 was measured by plethysmometry.

Figure 3:
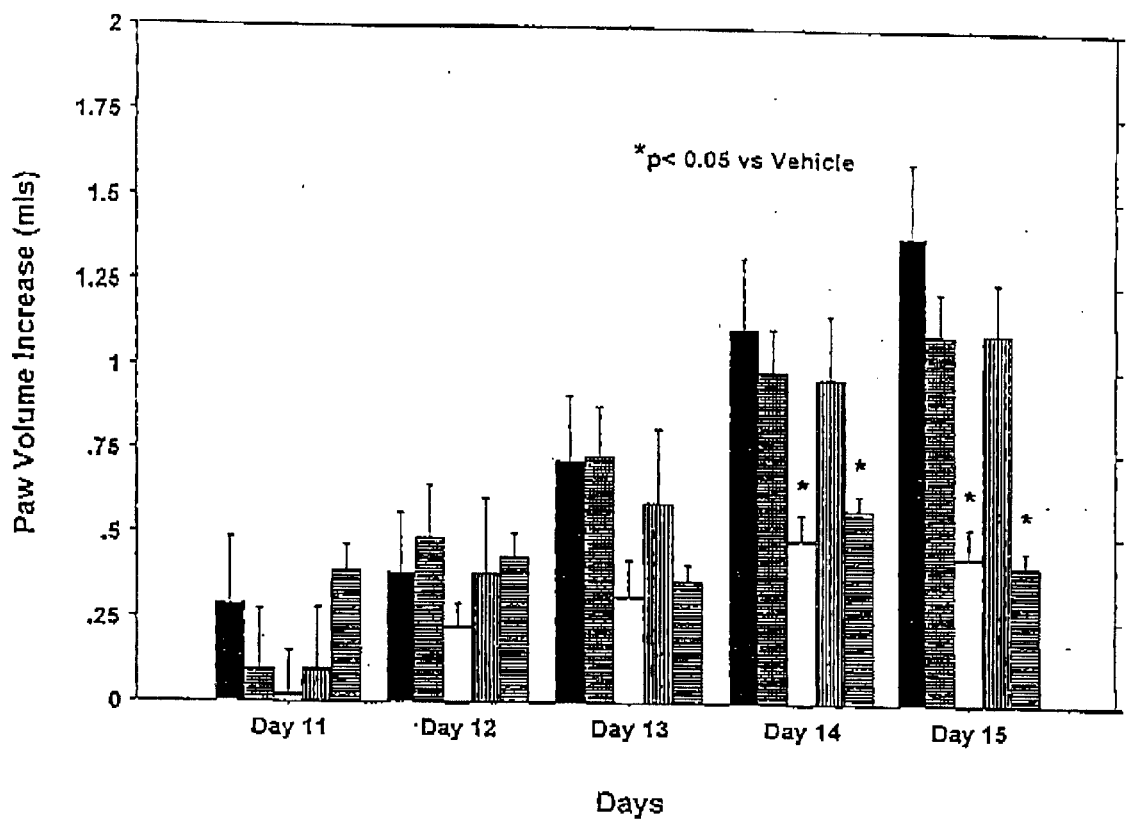
FIG. 3 illustrates the effectiveness of Naproxen prodrug according to the invention in the treatment of adjuvant-induced arthritis in a rat model system. Thus, paw volume increases (measured with a Plethysmometer) are reported as a function of time, and were measured in the injected feet of Lewis male rats in which arthritis was induced by intradermel injection of adjuvant into the footpad. Rats were injected on day 0 and treated once orally with either vehicle, naproxen or Naproxen prodrug on days 5–8 and 11–14. Blackened boxes represent animals treated with vehicle (5% DMSO/CMC); checkered boxes represent animals treated with naproxen at 1 mg/kg, open boxes represent animals treated with naproxen at 10 mg/kg, vertically lined boxes represent animals treated with Naproxen prodrug at 1.8 mg/kg (molar equivalent of 1 mg/kg naproxen alone), and horizontally lined boxes represent animals treated with Naproxen prodrug, at 18 mg/kg (molar equivalent of 10 mg/kg naproxen alone).

Rats were dosed daily by by oral gavage with 5 ml/kg of naproxen at 1 and 10 mg/kg and equimolar doses of Naproxen—containing conjugate of the invention (1.8 and 18 mg/kg) on days 5–8 and 11–14. The high doses of both drugs produced a comparable reduction of swelling on days 13 through 15 (FIG. 3), with a reduction compared to control of approximately 70% by day 15. The lower doses also appeared to have a slight effect by day 15. The results show that equimolar doses of Naproxen—containing conjugate of the invention resulted in antiinflammatory effects equal to those of naproxen in this model.

EXAMPLE 19
Pharmacokinetics of Naproxen in Plasma Following Intravenous Administration of Naproxen in Rats or Naproxen—Containing Conjugates of the Invention Naproxen is a nonsteroidal anti-inflammatory drug (NSAID) that is widely used in the treatment of rheumatoid arthritis, osteoarthritis, juvenile arthritis, ankylosing spondylitis, tendinitis and bursitis, and acute gout. Naproxen sodium, the sodium salt of naproxen, has also been developed as an analgesic because it is more rapidly absorbed. The side effects of GI ulceration, bleeding, and perforation is problematic to naproxen and NSAID therapy in general. Therefore, any therapeutic approach that decreases the side effects of naproxen could widen the usage of this therapy in treating inflammatory diseases.

The test articles utilized were Naproxen—containing conjugates of the invention (Medinox, Inc., San Diego) stored as a powder (at 4° C.) and naproxen (Sigma, St. Louis) stored at room temperature. On the day of animal dosing, test articles were freshly prepared in the mixture of carboxymethylcellulose (Sigma, St. Louis) and dimethylsulfoxide (Sigma, St. Louis) or water for injection.

Rats were catheterized using the carotid artery and jugular vein. The catheters were flushed with 30% polyvinylpyrrolidone (400 U/mL of heparin) to prevent clotting in the tip. 250 μL blood samples were collected by unhooking the flush syringe and letting the blood flow freely into centrifuge tubes at predetermined time points (see Table 1). The tubes were centrifuged at 13,000 rpm for 10 min at 4° C. All plasma samples were analyzed for naproxen content on the same day of collection.

A 50 μL aliquot of plasma sample was mixed with 100 μL of acetonitrile. After vortexing and centrifugation, 100 μL of supernatant was collected and added to 150 μL of 50 mM phosphate buffer (pH 5.0). After vortexing and centrifugation, 25 μL of supernatant was analyzed for naproxen by HPLC using a UV detector.

Pharmacokinetic analysis: The average plasma concentration at each time point was calculated and utilized in a pharmacokinetic analysis. Compartmental or noncompartmental pharmacokinetic analyses were performed using the WinNonlin program to calculate the following parameters: maximum concentration at 2 minutes ($C_{max}$), time to maximum concentration ($T_{max}$), area under the curve from zero to the last time point ($AUC_{last}$), area under the curve from zero to infinite time ($AUC_{inf}$), terminal phase half life (Beta-$t_{1/2}$), total plasma clearance (CL), and volume distribution at steady state ($V_{ss}$).

TABLE 1

Rat group assignment and doses

| Test Article | Group # | Rat # | Dose (mg/kg) | Plasma Sample Time |
|---|---|---|---|---|
| Naproxen | 2 | 1, 2, 3, & 4 | IV (0.55 mg/kg) | 5 min, 0, 5, 1, 2, 3, 4, 5, 6, 7, & 8 hrs |
| Naproxen prodrug | 1 | 1, 2, 3, & 4 | IV (1 mg/kg) | 5 min, 0.5, 1, 2, 3, 4, 5, 6, 7, & 8 hrs |

Note that 1 mg of Naproxen prodrug contains 0.55 mg of naproxen.

Figure 4:
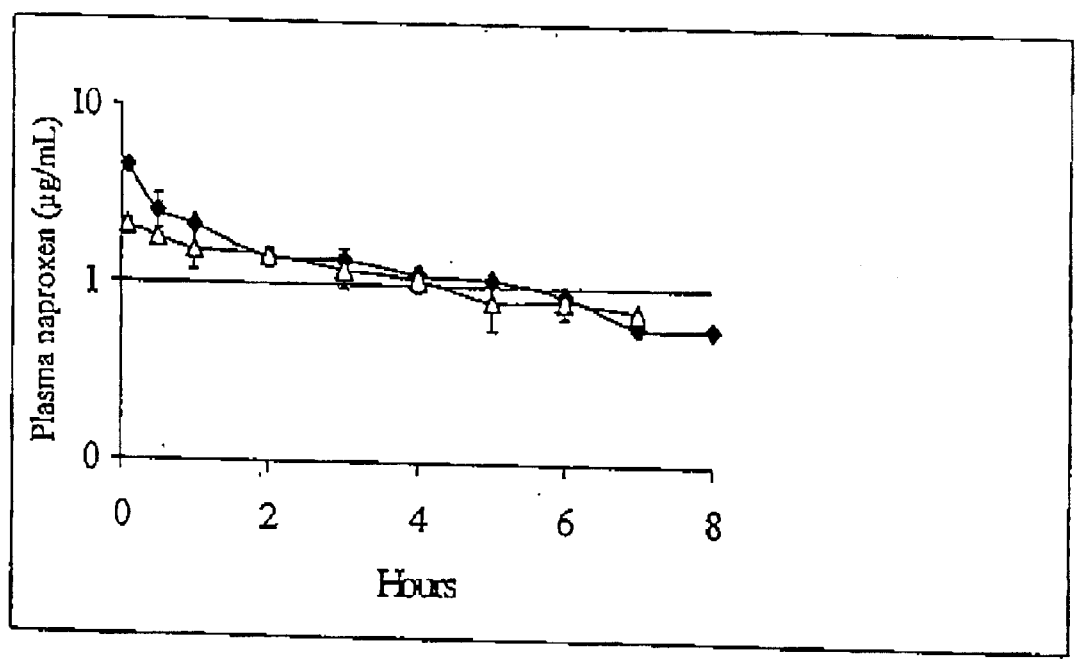
FIG. 4 presents concentration versus time curves for naproxen following IV administration of naproxen or Naproxen prodrug according to the invention. Blackened rectangles represent plasma concentration of naproxen following IV administration of 0.55 mg/kg of naproxen and open triangles represent plasma concentration of naproxen following IV administration of 1.1 mg/kg of Naproxen prodrug. After IV administration of naproxen, the naproxen plasma concentrations declined in a bi-exponential manner. The decline of plasma naproxen following Naproxen prodrug administration was monophonic. Note the lower plasma $C_{max}$ shown for Naproxen prodrug.

FIG. 4 presents the naproxen plasma concentration-time curves. After IV administration of naproxen, the naproxen plasma concentrations declined with bi-exponential manner (blackened rectangles), while the decline of Naproxen prodrug was monophasic (opened triangles). Table 2 shows the naproxen pharmacokinetic parameters. Both sets of pharmacokinetic parameters were similar except (5.39 and 1.98 μg/mL for naproxen and Naproxen prodrug administration, respectively). This slow release of naproxen from Naproxen prodrug might be advantageous in helping to reduce naproxen's side effects by slowing the rise of plasma $C_{max}$. In addition, the results show clearly that when administered intravenously, naproxen is released from Naproxen prodrug and appears in the circulation.

TABLE 2

Naproxen plasma pharmacokinetic parameters (n = 4, pooled data) after IV administration of Naproxen prodrug or naproxen in rats (compartmental analysis)

| Drug | Amount (mg/kg) | $C_{max}$ (μg/mL) | $AUC_{all}$ (μg*min/mL) | $AUC_{inf}$ (μg*min/mL) | $t_{1/2}$ (hrs) | CL (mL/hr*kg) | $V_{ss}$ (L/kg) |
|---|---|---|---|---|---|---|---|
| Naproxen | 0.55 | 5.39 | N/A | 14.60 | 4.36 | 38 | 0.22 |
| Naproxen prodrug | 1.00 | 1.98 | N/A | 12.70 | 4.44 | 43 | 0.28 |

EXAMPLE 20
Plasma Pharmacokinetics of Naproxen Following Oral Administration of Naproxen Prodrug or Naproxen in Rats The cannulated rats were separated into two groups as shown in Table 3. After oral gavage, the blood samples were withdrawn in various time points (Table 3) for HPLC analysis of naproxen levels.

TABLE 3

Rat group assignment and doses

| Test Article | Group # | Rat # | Dose (mg/kg) | Plasma Sample Time |
|---|---|---|---|---|
| Naproxen | 2 | 5, 6, 7, & 8 | oral (2.2 mg/kg) | 0.25, 0.5, 1, 3, 5, 7, 9, 11, 13 & 14 hrs |
| Naproxen prodrug | 1 | 1, 2, 3, & 4 | oral (4 mg/kg) | 0.25, 0.5, 1, 3, 5, 7, 9, 11, 13 & 14 hrs |

Note that 4 mg of the Naproxen prodrug contains 2.2 mg of naproxen.

Figure 5:
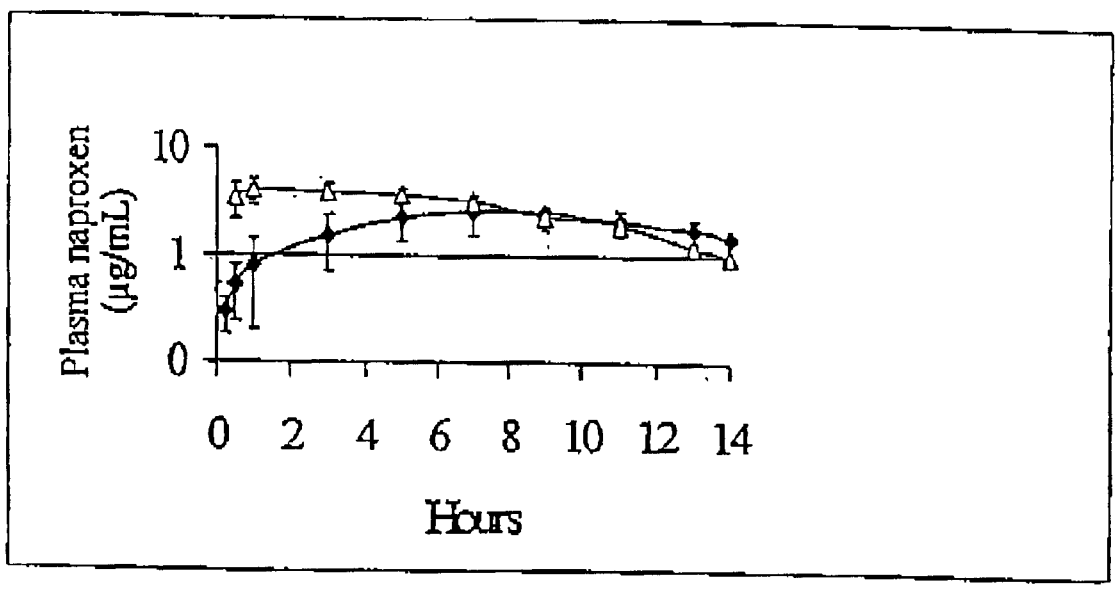
FIG. 5 presents concentration versus time curves for naproxen following oral administration of naproxen or Naproxen prodrug according to the invention. Open triangles represent plasma concentration of naproxen following oral administration of 2.2 mg/kg of naproxen and blackened rectangles represent plasma concentration of naproxen following oral administration of 4 mg/kg of Naproxen prodrug. Following oral administration of Naproxen prodrug, the time to maximum concentration of naproxen in plasma was considerably longer compared to naproxen administration ($T_{max}$ of 6.4 and 1.3 hours for Naproxen prodrug and naproxen, respectively). The corresponding $C_{max}$ values were 2.34 and 4.82 μg/mL for Naproxen prodrug and naproxen, respectively. There was no significant difference for $AUC_{nif}$ values.

FIG. 5 presents the naproxen plasma concentration-time curves (after oral administration of naproxin (open triangles) and naproxen prodrug (blackened rectangles). Following oral administration of Naproxen prodrug, the time to maximum naproxen plasma levels was considerably delayed compared to naproxen ($T_{max}$ of 1.3 and 6.4 hours for Naproxen prodrug and naproxen, respectively) (Table 4). The corresponding $C_{max}$ values were 2.34 and 4.05 a$\mu$g/mL, respectively. There was no significant difference for $AUC_{inf}$ values. The lower $C_{max}$, longer $T_{max}$, and similar $AUC_{inf}$ of Naproxen prodrug could be significant factors in reducing the side effects of naproxen.

TABLE 4

Naproxen plasma pharmacokinetic parameters (n = 4, pooled data) after oral administration of Naproxen prodrug or naproxen in rats (compartmental analysis)

| Drug | Dose (mg/kg) | $C_{max}$ ($\mu$g/mL) | $T_{max}$ (hrs) | $AUC_{all}$ ($\mu$g*hr/mL) | $AUC_{inf}$ ($\mu$g*hr/mL) | $t_{1/2}$ (hrs) |
|---|---|---|---|---|---|---|
| Naproxen | 2.2 | 4.82 | 1.3 | N/A | 48.4 | 6.0 |
| Naproxen prodrug | 4 | 2.34 | 6.4 | N/A | 45.6 | 7.5 |

Based on plasma data, Naproxen prodrug by oral or IV administration, produces better naproxen pharmacokinetic profiles than naproxen itself.

While the invention has been described in detail with reference to certain preferred embodiments thereof, it will be understood that modifications and variations are within the spirit and scope of that which is described and claimed.

That which is claimed is:

1. A compound comprising a nitric oxide scavenger covalently linked to a pharmacologically active agent, wherein said covalent linkage is selected from ester, sulfate ester, sulfonate ester, phosphate ester, or carbonate ester.

2. A compound according to claim 1 wherein said nitric oxide scavenger is a dithiocarbamate.

3. A compound according to claim 2 wherein said dithiocarbamate moiety is sarcosine dithiocarbamate, iminodiacetic acid dithiocarbamate, diethyldithiocarbamate, diisopropyldithiocarbamate, sugar-linked dithiocarbamates, pyrrolidine dithiocarbamate or proline dithiocarbamate.

4. A compound according to claim 1 wherein said covalent linkage is an ester linkage.

5. A compound according to claim 1 wherein said covalent linkage is a sulfonate ester linkage.

6. A compound according to claim 1 wherein said covalent linkage is a sulfate ester linkage.

7. A compound according to claim 1 wherein said covalent linkage is a phosphate ester linkage.

8. A compound according to claim 1 wherein said pharmacologically active agent is selected from NSAIDs, analgesics/antipyretics, sedatives/hypnotics, antianginal agents, antianxiety agents, antidepressants, antipsychotic agents, antimanic agents, antiarrhythmics, antihypertensive drugs, antihistamine/antipruritic drugs, immunosuppressants, antimetabolite cytotoxics, neuroprotective agents, T cell inhibitors, antimigraine agents, antiarthritic agents, antigout agents, anticoagulants, thrombolytic agents, antifibrinolytic agents, hemorheologic agents, antiplatelet agents, anticonvulsants, agents useful for calcium regulation, antibacterial agents, antifungal agents, antiviral agents, antimicrobials, anti-infectives, bronchodialators, hormones, hypoglycemic agents, hypolipidemic agents, proteins, nucleic acids, agents useful for erythropoiesis stimulation, antiulcer/antireflux agents, antinauseants/antiemetics, septic shock agents, multiple sclerosis agents, organ transplantation agents, systemic lupus erythematosus (SLE) agents, Alzheimer's disease agents, antiparkinson agents, psoriasis agents, diabetes agents, stroke agents, agents useful for the treatment of carcinomas, agents useful for the treatment of endometriosis, agents useful for the treatment of uterine contraction, agents useful for the treatment of diuresis, agents useful for the treatment of cystic fibrosis, agents useful for the treatment of neutropenia, agents useful for the treatment of lung cancer, agents useful for the treatment of respiratory disorders, agents useful for the treatment of ischemia/reperfusion injury, agents useful for the treatment of ophthalmic diseases, agents useful for the treatment of cardiovascular diseases, anti-inflammatory agents or antioxidants.

9. A compound according to claim 1 wherein said pharmacologically active agent is a non-steroidal antiflammatory drug, an antihypertensive agent, an antineoplastic agent, an anti-allograft rejection agent, a neuroprotective agent, an immunosuppressive agent or an antioxidant.

10. A compound according to claim 1 wherein said pharmacologically active agent is aspirin, ibuprofen, ketoprofen, naproxen, diclofenac, adriamycin, cyclosporin, FK506, LFA-1, selectin inhibitors, tissue plasminogen activator or lubeluzole.

11. A composition comprising a compound according to claim 1 in a pharmaceutically acceptable carrier therefor.

12. A composition according to claim 11 wherein said pharmaceutically acceptable carrier is selected from a solid, solution, emulsion, dispersion, micelle or liposome.

13. A composition according to claim 11 wherein said composition further comprises an enteric coating.

14. In the administration of a pharmacologically active agent to a subject for treatrnent of a pathological condition, the improvement comprising covalently attaching a suitable nitric oxide scavenger to said pharmacologically active agent prior to administration of said pharmacologically active agent to said subject.

15. In the treatment of a subject suffering from a pathological condition by administration thereto of a pharmacologically active agent, the improvement comprising covalently attaching a suitable nitric oxide scavenger to said pharmacologically active agent prior to administration thereof to said subject.

16. A method for the treatment of a subject afflicted with a pathological condition, said method comprising administering to said subject an effective amount of a modified pharmacologically active agent, wherein said pharmacologically active agent is effective for treatment of said condition, and wherein said pharmacologically active agent has been modified by the covalent attachment thereto of a suitable nitric oxide scavenger.

17. A method for the preparation of a protected form of a pharmacologically active agent, said method comprising covalently attaching a suitable nitric oxide scavenger to said pharmacologically active agent.

18. A method for reducing the side effects induced by administration of a pharmacologically active agent to a subject, said method comprising covalently attaching a suitable nitric oxide scavenger to said pharmacologically active agent prior to administration to said subject.

19. A method for enhancing the effectiveness of a pharmacologically active agent, said method comprising covalently attaching a suitable nitric oxide scavenger to said pharmacologically active agent.

20. A compound according to claim 10 wherein said pharmacologically active agent is naproxen.

21. A compound according to claim 20 having the structure:

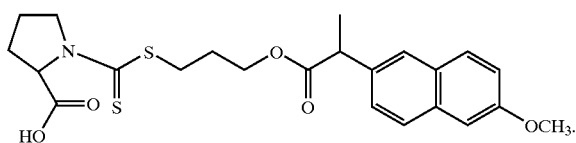

* * * * *